(12) United States Patent
Bowers et al.

(10) Patent No.: US 6,468,974 B1
(45) Date of Patent: Oct. 22, 2002

(54) COMPOUNDS HAVING GROWTH HORMONE RELEASING ACTIVITY

(75) Inventors: Cyril Y. Bowers, New Orleans, LA (US); Frank Momany, Peoria, IL (US); Yongwu Liang, Sprin, TX (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 09/370,111

(22) Filed: Aug. 6, 1999

Related U.S. Application Data

(60) Provisional application No. 60/096,795, filed on Aug. 14, 1998, and provisional application No. 60/129,806, filed on Apr. 16, 1999.

(51) Int. Cl.[7] .......................... A61K 38/00; C07K 5/00; C07K 7/00
(52) U.S. Cl. .............................. 514/16; 514/12; 514/15; 530/300
(58) Field of Search .................. 530/300; 514/15, 514/16, 12

(56) References Cited

U.S. PATENT DOCUMENTS

| | | | |
|---|---|---|---|
| 4,223,019 A | 9/1980 | Momany | 424/177 |
| 4,223,020 A | 9/1980 | Momany | 424/177 |
| 4,223,021 A | 9/1980 | Momany | 424/177 |
| 4,224,316 A | 9/1980 | Momany | 424/177 |
| 4,226,857 A | 10/1980 | Momany | 424/177 |
| 4,228,155 A | 10/1980 | Momany | 424/177 |
| 4,228,156 A | 10/1980 | Momany | 424/177 |
| 4,228,157 A | 10/1980 | Momany | 424/177 |
| 4,228,158 A | 10/1980 | Momany | 424/177 |
| 4,410,512 A | 10/1983 | Bowers | 424/177 |
| 4,410,513 A | 10/1983 | Momany | 424/177 |
| 5,486,505 A | 1/1996 | Bowers | 514/16 |
| 5,492,916 A | 2/1996 | Morriello | 514/318 |
| 5,492,920 A | 2/1996 | Chen | 514/323 |
| 5,494,919 A | 2/1996 | Morriello | 514/323 |
| 5,622,973 A | 4/1997 | Moriello | 514/318 |
| 5,663,146 A | 9/1997 | Bowers | 514/16 |
| 5,776,901 A | 7/1998 | Bowers et al. | |

FOREIGN PATENT DOCUMENTS

| | | |
|---|---|---|
| EP | 0 083 864 | 7/1983 |
| WO | WO 93/04081 | 3/1993 |
| WO | WO 94/07519 | 4/1994 |
| WO | WO95/13069 | 5/1995 |
| WO | WO96/15148 | 5/1996 |
| WO | WO96/35713 | 11/1996 |
| WO | WO97/00894 | 1/1997 |
| WO | WO97/07117 | 2/1997 |
| WO | WO97/11697 | 4/1997 |
| WO | WO97/22367 | 6/1997 |

OTHER PUBLICATIONS

Deghenghi, R., Structural Requirements of Growth Hormone Secretagogues, (1997) International Symposium, pp. 27–35.

Deghenghi, R., et al., Small Peptides as Potent Releasers of Growth Hormone, (1995) *J. of Ped Endocrinology & Metabolism*, 8:311–313.

Deghenghi, R., et al., GH–Releasing Activity of Hexarelin, a New Growth Hormone Releasing Peptide, in Infant and Adult Rats, (1994) *Life Sciences*, 54:1321–1328.

*Primary Examiner*—Christopher S. F. Low
*Assistant Examiner*—David Lukton
(74) *Attorney, Agent, or Firm*—Nixon & Peabody LLP

(57) ABSTRACT

Compounds that promote growth hormone releasing activity are disclosed. These compounds have the formula:

$$A_1\text{-}A_2\text{-}X;\ Al_1\text{-}X';\ \text{or}\ A_{1''}\text{-}Y$$

These compounds can be present in a pharmaceutical composition. The compounds can be used with a second compound that acts as an agonist at the growth hormone releasing hormone receptor or which inhibits the effects of somatostatin. These compounds can be used for a variety of uses such as treating hypothalamic pituitary dwarfism, osteoporosis, burns, or promoting wound healing.

21 Claims, No Drawings

COMPOUNDS HAVING GROWTH HORMONE RELEASING ACTIVITY

This application claims the benefits of provisional application No. 60/096,795, filed Aug. 14, 1998 and No. 60/129,806, filed Apr. 16, 1999.

FIELD OF THE INVENTION

This invention relates to novel compounds that promote the release of growth hormones when introduced to animals, preferably humans, and methods of use thereof.

BACKGROUND OF THE INVENTION

The elevation of growth hormone (GH) levels in animals, e.g., mammals including humans, upon administration of GH-releasing compounds can lead to enhanced body weight and to enhanced milk production if sufficiently elevated GH levels occur upon administration. Further, it is known that the elevation of growth hormone levels in mammals and humans can be accomplished by application of known growth hormone releasing agents, such as the naturally occurring growth hormone releasing hormones.

The elevation of growth hormone levels in mammals can also be accomplished by application of growth hormone releasing peptides (GHRPs), some of which have been previously described, for example, in U.S. Pat. Nos. 4,223,019; 4,223,020; 4,223,021; 4,224,316; 4,226,857; 4,228,155; 4,228,156; 4,228,157; 4,228,158; 4,410,512; 4,410,513.

Antibodies to the endogenous growth hormone release inhibitor, somatostatin (SRIF) have also been used to cause elevated GH levels. In this latter example, growth hormone levels are elevated by removing the endogenous GH-release inhibitor (SRIF) before it reaches the pituitary, where it inhibits the release of GH.

These methods for promoting the elevation of growth hormone levels frequently involve materials which are expensive to synthesize and/or difficult to isolate in sufficient purity for administration to a target animal. Low molecular weight, relatively simple and inexpensive compounds that have the ability to promote the release of growth hormone would be desirable in that they could be readily and inexpensively prepared, easily modified chemically and/or physically, as well as easily purified and formulated, and designed to have improved transport properties.

GH and/or GHRPs have been administered to stimulate growth hormone production and/or release, for example, to stimulate growth, enhance milk production, enhance body weight, increase rate of protein synthesis, reduce rate of carbohydrate utilization, increase mobilization of pre-fatty acids. Although the use of many of these compounds such as a series of short peptides (e.g., U.S. Pat. Nos. 5,663,146 and 5,486,505) have been important steps in the design and delivery of compounds having GH and/or GHRP properties, improvements can still be made. For example, improvements can be made in the areas of oral bioavailability, serum retention time, etc.

Non-peptidal or hybrid-peptidal secretagogues have also been described. See U.S. Pat. Nos. 5,494,919; 5,492,920; 5,492,916; 5,622,973; WO95/13069, WO96/15148; WO96/35713; WO97/22367; WO97/00894; WO97/07117; and WO97/11697. Despite the general descriptions of such compounds, it is not possible to make broad generalizations about which particular compounds are favorable. Although some secretagogues, which can promote the release and elevation of growth hormone levels in the blood, have been described, corresponding data on the biological activity has often been lacking. Moreover, even in terms of tripeptides with or without C-terminal modifications, the data suggests that it has heretofore been impossible to make the broad sweeping generalization made in those publications about what would or would not be a favorable amino acid combination at the three positions of a tripeptide holding the C-terminal constant or holding the peptidal portion constant while making changes, or changing the chemical moieties added. Changes in any of the constituents can have great effects on activity. It is submitted that these references do not lead to general teachings of biological efficacy.

In order to maximize the ability to select and tailor a compound, it would be desirable to have a class of compounds that generally provide good growth hormone releasing effects and have at least one other desirable biological activity such as better bioavailability, absorption, metabolism, pharmacokinetics, excretions, etc. It would also be desirable to have compounds which can promote the release and elevation of growth hormone levels in the blood of animals, particularly in humans, to be able to use such compounds to promote the release and/or elevation of growth hormone levels in the blood of animals and humans, and to provide methods for promoting the release and/or elevation of growth hormone levels in the blood of animals using such compounds.

The aforementioned discussion illustrates that a broad chemical diversity of synthetic GHRPs ranging from peptides to partial peptides to non-peptides. Overall, the peptides and partial peptides have been the most effective in promoting elevated growth hormone levels. For example, partial peptides consisting of natural and unnatural amino acids of different chain lengths and C-terminal amide groups or a substituted amide with various organic chemical groups. Results published as early as 1982 stated that certain GHRPs with only 3–7 amino acids released GH and that having a D-amino acid at certain positions was useful. From 1982 to the present, GHRPs with more potent GH releasing activity have been developed. This research taught that certain amino acid positions could have certain substitutions but not others, and that one amino acid residue could affect what other substitutions could be made.

Until compounds having the optimum physical-chemical properties and physiological-biological actions and effects are discovered for various diagnostic and therapeutic uses in humans, it is important to discover a general chemical approach that will result in new types of GHRPs. Such a broader GHRP chemical base will make it possible to better implement and refine the GHRP approach.

Properties of GHRPs that are important include that they are effective when administered orally. In addition, the compound should augment the normal pulsatile physiological secretion of GH. In some subjects with decreased GH secretion, GH can be replaced in a physiological way. Physiological replacement of a hormonal deficiency improves health while minimizing the potential adverse action of the hormone. This is especially important in treating older men and women, as they may be particularly susceptible to the adverse effects of over-treatment with GH. Already, chronic administration of GHRPs to animals and humans has produced anabolic effects. Body weight gain has been increased in rats, milk production has been increased in cows. Additionally, when a compound such as DAla-DβNal-Ala-Trp-DPhe-Lys-$NH_2$ (GHRP-2) was administered to short-statured children with various degrees of GH deficiency 2–3 times per day over a 2 year period, the rate of height velocity has been accelerated in those children.

In principle, the anabolic biological effects of GHRPs emphasize the potential clinical value of the GHRP approach. The finding that GHRP-2 is less effective on height velocity than usually obtained with chronic recombinant human growth hormone (rhGH) administration, underscores the desirability for improving the GHRP approach. This includes further optimization and extension of the range of the GHRP chemistry in order to produce more effective biological actions.

In looking at these compounds, one looks at a varied series of biological effects such as the duration of action of GHRP. Other parameters that may substantially be affected by the chemistry of the GHRP include desensitization of the GHRP GH response, actions on the hypothalamus, effects on SRIF release and action, effects on ACTH and PRL release as well as possible effects on putative subclasses of GHRP receptors. All of these actions are directly and/or indirectly dependent on the GHRP chemistry, pattern and efficiency of oral absorption as well as the metabolism and secretion of the particular GHRP.

SUMMARY OF THE INVENTION

We have now discovered a new group of compounds (sometimes referred to as secretagogues) that provide desirable in vitro and in vivo growth hormone releasing activity and have at least one other desirable biological activity such as increased retention time. These compounds have the following formulas:

$$A_1\text{-}A_2\text{-}X \qquad \text{Formula I}$$

wherein $A_1$ is Aib (aminoisobutyric acid), inip (isonipecotyl) or ABU (aminobutyric acid). The Aib residue can be substituted or unsubstituted. Preferred substituents include $C_1$–$C_6$ alkyl and halogens. Aib is preferably unsubstituted. Aib is preferably αAib. ABU is preferably γABU or αγABU, more preferably α,γABU;

$A_2$ is any natural L-amino acid or Pal, or their respective D-isomers, DαNal (α-naphthyl-D-alanine) or DβNal (β-naphthyl-D-alanine), preferably $A_2$ is DTrp, DαNal (α-naphthyl-D-alanine) or DβNal (β-naphthtyl-D-alanine), more preferably $A_2$ is DTrp or DαNal;

X is
  (1) $R_1$-$R_2$-Z, wherein $R_1$ and $R_2$ are any natural L-amino acid, Pal, αNal, βNal, DpCl, CHx, where $CH_x$ is cyclohexyl, CHxAla, or any of their respective D-isomers, preferably $R_1$ is DPro, DTrp, DβNal or DPhe, more preferably $R_1$ is DPro or DTrp; and $R_2$ is preferably Gly, Phe, Pro, DPro, DPhe, DPal, DLeu, DHis, DVal, DGln, DArg, DAla, DSer, DThr, DIle, Arg, Orn Lys, Ala, Pal, Thr, Val, PheCHx, CHxAla or CHx, where x is preferably 1–8, more preferably 1 to 5; and Z is $CONH_2$ or COOH;
  (2) $DpR_3Phe$-$R_4$-Z, wherein $R_3$ is a halogen, preferably Cl, and $R_4$ is any natural L-amino acid or Pal, or their respective D-isomers, preferably $R_4$ is Phe or Arg, and Z is $CONH_2$ or COOH;
  (3) $NH(CH_2)_nNH$, where n is 1 to 8, such as -2-aminoethylamide, -3-aminopropylamide, -4-aminobutylamide, -5-aminopentylamide, or -6-aminohexylamide;
  (4) $R_5$-$R_6$, wherein $R_5$ is any natural L-amino acid, Pal, αNal, βNal, DpCl, CHx where x is 1 to 10, or any of their respective D-isomers, preferably $R_5$ is DPro or DTrp, and $R_6$ is (a) diisobutylamide
  (b) dipropylamide
  (c) butylamide
  (d) pentylamide
  (e) dipentylamide
  (f) C(=O) (substituted heteroalicyclic or heteroaromatic) such as
     -piperidine-3-methylbenzylether
     -N-diethylnipectamide
     -N-piperazine methylsulfonamide
     -diethylamide
     -m-methylpiperidine
     -3,3-diphenylpropylamide
     -4-piperidino piperidinamide
     -4-phenyl-piperidinamide
     -N-methylpiperazine
     -2-morpholinoethylamine
     -spiroindole methylsulfonamide
     -pyrrolidine amide
     -indoleamide
     -3-piperidine methanolamide
     -tropin amide
     -2-aminoethylamide
     -3-aminopropylamide
     -4-aminobutylamide
     -5-aminopentylamide
     -6-aminohexylamide;
  (5) DTrp Phe $ArgR_7$, wherein $R_7$ is $NH(CH_2)_nNH$, where n is 1 to 8, such as -2-aminoethylamide, -3-aminopropylamide, -4-aminobutylamide, -5-aminopentylamide, or -6-aminohexylamide; or
  (6) $R_8$-$R_9$-$R_{10}$-Z, wherein $R_8$ is DTrp, DPro, DαNal or DβNal, preferably $R_8$ is DTrp or DPro, $R_9$ is any natural L-amino acid or Pal, or their respective D-isomers, preferably $R_9$ is Phe, DVal, DPro, DIle, Ile, more preferably Ris Phe, DVal or DPro; $R_{10}$ is any natural L-amino acid or Pal, or their respective D-isomers, preferably $R_{10}$ is Lys or Arg, and Z is $CONH_2$ or COOH, preferably Z is $CONH_2$.

$$A_{1'}\text{-}X' \qquad \text{Formula II:}$$

wherein $A_{1'}$ is Aib, inip, ABU, IMC (imidazole carboxylic acid), Ava, 4-IMA (Nα-imidazole acetic acid), βAla, Ileu, Trp, His, DpCl, CHx, or any of their respective D-isomers. The Aib residue can be substituted or unsubstituted. Preferred substituents include N- and N-,N-$C_1$–$C_6$ alkyl, halogens, N- and N-,N-2 hydroxyethyl, 3-hydroxypropyl, 4-hydroxybutyl and 3-hydroxyisobutyl. Aib is preferably unsubstituted. Aib is preferably αAib. ABU is preferably γABU or αγABU, more preferably α,γABU; and X' is
  (1) $R_{1'}$-$R_{2'}$-Z, wherein $R_{1'}$ is any natural L-amino acid or Pal, or their respective D-isomers, DαNal or DβNal, preferably $R_{1'}$ is DTrp, DαNal or DβNal, more preferably $R_{1'}$ is DTrp or DαNal, and $R_{2'}$ is any natural L-amino acid, Pal, αNal, βNal, DpCl, Aib, preferably αAib, CHx where x is 1 to 10, or CHxAla, or any of their respective D-isomers, and Z is $CONH_2$ or COOH, preferably Z is $CONH_2$; or
  (2) $R_{3'}$-$R_{4'}$, wherein $R_{3'}$ is any natural L-amino acid or Pal, or their respective D-isomers, DαNal or DβNal, preferably $R_3$ is DPro, DTrp, DαNal or DβNal, more preferably $R_{3'}$ is DPro, DTrp or DαNal, and $R_{4'}$ is $NH(CH_2)_nNH$, where n is 1 to 8, such as -2-aminoethylamide, -3-aminopropylamide, -4-aminobutylamide, -5-aminopentylamide, or -6-aminohexylamide.

The organic and inorganic addition salts thereof are also included.

In an alternative embodiment the compound has the formula $$A_{1''}\text{-}Y, \qquad \text{Formula III:}$$

wherein $A_{1''}$ is Aib, inip, ABU, βAla, His, Sar or any of their respective D-isomers. The Aib residue can be substituted or unsubstituted. Preferred substituents include N- and N-,N-$C_1$–$C_6$ alkyl, halogens, N- and N-,N-2 hydroxyethyl, 3-hydroxypropyl, 4-hydroxybutyl and 3-hydroxyisobutyl. Aib is preferably unsubstituted. $A_{1''}$ is preferably Aib, inip or ABU. More preferably Aib is αAib. Abu is preferably γAbu or α,γAbu, more preferably α,γAbu.

Y is $A_{2'}$-$A_3$-$A_4$-$A_5$-$A_6$-Z',
$A_{2'}$-$A_3$-$A_4$-$A_5$-Z' or $A_{2'}$-$A_3$-$A_4$-Z'
  wherein $A_{2'}$ is $A_5$-$A_{2''}$ or $A_{2''}$,
  wherein $A_5$ is a spacer amino acid such as His,
  $A_{2''}$ is as defined above for $A_2$. $A_{2''}$ is preferably DTrp, DαNal or DβNal. $A_{2''}$ is more preferably DTrp.
  $A_3$, $A_4$ and $A_5$ are any natural L-amino acid, Pal, αNal, βNal, Nle, Arg-DPro, DPCl, D or L (CHX), cyclohexylalanine (CHXAla), or any of their respective D-isomers, preferably $A_3$ is DPro, DTrp, DβNal or DPhe, more preferably $A_3$ is DPro or DTrp; and $A_4$ is preferably Gly, Phe, Pro, Ile, DPro, DPhe, DPal, DLeu, DHis, DVal, DGln, DIle, DNle, DArg, DAla, DSer, DThr, DIle, Arg, Orn Lys, Ala, Pal, Thr, Val, PheCHX, CHXAla or CHX. $A_4$ is preferably DSer, DAug, DPro, DTrp, DVal, DIle, DThr, DNVal, DNle, Ile, Pro, Phe and still more preferably, $A_4$ is DPro. $A_5$ is preferably Ile, Arg, Pal, DArg, DSer, Lys and Arg-DPro. More preferably $A_5$ is Arg, DArg, and Lys.
  Z' is $NH_2$, OH or alkylamino or aminoalkylamino, preferably the alkylamino is NH ($C_1$–$C_{10}$ alkyl) e.g. $NH(CH_2)_nCH_3$, where n is 1 to 10 such as

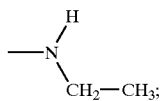

N di-($C_1$–$C_{10}$ alkyl) e.g., N di-$(CH_2)_nCH_3$ such as

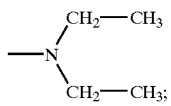

preferably the aminoalkylamino is a NH ($C_1$–$C_{10}$ alkylamino, e.g. $NH(CH_2)_nNH_2$ such as

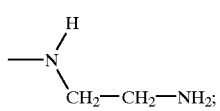

N (di $C_1$–$C_{10}$ alkylamino), e.g., N[di-$(CH_2)_nNH_2$] such as

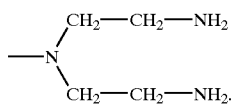

These compounds can be administered to an animal to promote release of serum growth hormone levels. Thus, these secretagogues can be used in a range of methods for example, to increase milk production, enhance body growth, treat hypothalmic pituitary dwarfism, osteoporosis, burns and renal failure, and to promote wound healing. They can also be used diagnostically. For example, to discover a loss of growth hormone receptor functioning.

DETAILED DESCRIPTION OF THE INVENTION

The compounds described herein are typically easy to synthesize, have efficacy at promoting an increase in serum growth hormone levels, and are desirable for large scale production and utilization. In addition, these compounds may be advantageous in having physiochemical properties which are desirable for the efficient delivery of such polypeptide compounds to a wide variety of animal species because of an improvement in at least one of bioavailability, absorption, metabolism, pharmacokinetics and excretion. The preferred methods of delivery are oral, nasal and continuous delivery utilizing special chemical/mechanical methods of delivery. Pulsed therapy is one preferred method of administration. These compounds have either of the following two formulas:

$$A_1\text{-}A_2\text{-}X \qquad \text{Formula I:}$$

wherein $A_1$ is Aib (aminoisobutyric acid), inip (isonipecotyl) or ABU (aminobutyric acid). The Aib residue can be substituted or unsubstituted. Preferred substituents include $C_1$–$C_6$ alkyl and halogens. Aib is preferably unsubstituted. Aib is preferably αAib. ABU is preferably γABU or αγABU, more preferably α,γABU;

$A_2$ is any natural L-amino acid or Pal, or their respective D-isomers, DαNal (α-naphthyl-D-alanine) or DβNal (β-naphthtyl-D-alanine), preferably $A_2$ is DTrp, DαNal (α-naphthyl-D-alanine) or DβNal (β-naphthyl-D-alanine), more preferably $A_2$ is DTrp or DαNal;

X is
(1) $R_1$-$R_2$-Z, wherein $R_1$ and $R_2$ are any natural L-amino acid, Pal, αNal, βNal, DpCl, CHx, CHxAla, or any of their respective D-isomers, preferably $R_1$ is DPro, DTrp, DβNal or DPhe, more preferably $R_1$ is DPro or DTrp; and $R_2$ is preferably Gly, Phe, Pro, DPro, DPhe, DPal, DLeu, DHis, DVal, DGln, DArg, DAla, DSer, DThr, DIle, Arg, Orn Lys, Ala, Pal, Thr, Val, PheCHx, CHxAla or CHx, where x is preferably 1–8, more preferably 1 to 5; and Z is $CONH_2$ or COOH;
(2) $DpR_3$Phe-$R_4$-Z, wherein $R_3$ is a halogen, preferably Cl, and $R_4$ is any natural L-amino acid or Pal, or their respective D-isomers, preferably $R_4$ is Phe or Arg, and Z is $CONH_2$ or COOH;
(3) $NH(CH_2)_nNH$, where n is 1 to 8, such as -2-aminoethylamide, -3-aminopropylamide, -4-aminobutylamide, -5-aminopentylamide, or -6-aminohexylamide;
(4) $R_5$-$R_6$, wherein $R_5$ is any natural L-amino acid, Pal, αNal, βNal, DpCl, CHx where x is 1 to 10, or any of their respective D-isomers, preferably $R_5$ is DPro or DTrp, and $R_6$ is
(a) diisobutylamide
(b) dipropylamide
(c) butylamide
(d) pentylamide
(e) dipentylamide
(f) C(=O)(substituted heteroalicyclic or heteroaromatic) such as
-piperidine-3-methylbenzylether
-N-diethylnipectamide
-N-piperazine methylsulfonamide
-diethylamide
-m-methylpiperidine
-3,3-diphenylpropylamide
-4-piperidino piperidinamide
-4-phenyl-piperidinamide
-N-methylpiperazine
-2-morpholinoethylamine
-spiroindole methylsulfonamide
-pyrrolidine amide
-indoleamide
-3-piperidine methanolamide
-tropin amide
-2-aminoethylamide
-3-aminopropylamide
-4-aminobutylamide
-5-aminopentylamide
-6-aminohexylamide;
(5) DTrp Phe Arg $R_7$, wherein $R_7$ is $NH(CH_2)_nNH$, where n is 1 to 8, such as -2-aminoethylamide, -3-aminopropylamide, -4-aminobutylamide, -5-aminopentylamide, or -6-aminohexylamide; or
(6) $R_8$-$R_9$-$R_{10}$-Z, wherein $R_8$ is DTrp, DPro, DαNal or DβNal, preferably $R_8$ is DTrp or DPro, $R_9$ is any natural L-amino acid or Pal, or their respective D-isomers, preferably $R_9$ is Phe, DVal, DPro, DIle, Ile, more preferably $R_9$ is Phe, DVal or DPro; $R_{10}$ is any natural L-amino acid or Pal, or their respective D-isomers, preferably $R_{10}$ is Lys or Arg, and Z is $CONH_2$ or COOH, preferably Z is $CONH_2$.

$A_{1'}$-X'  Formula II:

wherein $A_{1'}$, is Aib, inip, ABU, IMC (imidazole carboxylic acid), Ava, 4-IMA (Nα-imidazole acetic acid), βAla, Ileu, Trp, His, DpCl, CHx, or any of their respective D-isomers. The Aib residue can be substituted or unsubstituted. Preferred substituents include N- and N-,N- $C_1$–$C_6$ alkyl, halogens, N- and N-,N-2 hydroxyethyl, 3-hydroxypropyl, 4-hydroxybutyl and 3-hydroxyisobutyl. Aib is preferably unsubstituted. Aib is preferably αAib. ABU is preferably γABU or αγABU, more preferably α,γABU; and
X' is
(1) $R_{1'}$-$R_{2'}$-Z, wherein $R_{1'}$ is any natural L-amino acid or Pal, or their respective D-isomers, DαNal or DβNal, preferably $R_{1'}$ is DTrp, DαNal or DβNal, more preferably $R_{1'}$ is DTrp or DαNal, and $R_{2'}$ is any natural L-amino acid, Pal, αNal, βNal, DpCl, Aib, preferably αAib, CHx where x is 1 to 10, or CHxAla, or any of their respective D-isomers, and Z is $CONH_2$ or COOH, preferably Z is $CONH_2$; or
(2) $R_{3'}$-$R_{4'}$, wherein $R_{3'}$ is any natural L-amino acid or Pal, or their respective D-isomers, DαNal or DβNal, preferably $R_{3'}$ is DPro, DTrp, DαNal or DβNal, more preferably $R_{3'}$ is DPro, DTrp or DαNal, and $R_{4'}$ is $NH(CH_2)_nNH$, where n is 1 to 8, such as -2-aminoethylamide, -3-aminopropylamide, -4-aminobutylamide, -5-aminopentylamide, or -6-aminohexylamide.

The organic and inorganic addition salts thereof are also included.

The abbreviations for the residues of amino acids used herein are in agreement with the standard nomenclature, and are set forth below:

Gly Glycine
Tyr L-Tyrosine
Ile L-Isoleucine
Glu L-Glutamic Acid
Thr L-Threonine

| | |
|---|---|
| Phe | L-Phenylalanine |
| Ala | L-Alanine |
| Lys | L-Lysine |
| Asp | L-Aspartic Acid |
| Cys | L-Cysteine |
| Arg | L-Arginine |
| Gln | L-Glutamine |
| Pro | L-Proline |
| Leu | L-Leucine |
| Met | L-Methionine |
| Ser | L-Serine |
| Asn | L-Asparagine |
| His | L-Histidine |
| Trp | L-Tryptophan |
| Val | L-Valine |
| Orn | L-Ornithine |

Moreover, all of the three letter-abbreviations of the amino acids preceded by a "D" indicate the dextro-isomer of the aminoacidic residue, and glycine is considered to be included in the term naturally occurring L-amino acids. Other abbreviations used herein include the following:

| | |
|---|---|
| Aib | aminoisobutyric acid |
| inip | isonipecotyl |
| ABU | aminobutyric acid |
| αNal | α-naphthyl alanine |
| βNal | β-naphthyl alanine |
| DαNal | α-naphthyl-D-alanine |
| DβNal | β-naphthyl-D-alanine |
| Pal | 3-pyridyl alanine |
| CHx | cyclohexyl |
| CHxAla | L-cyclohexylalanine |
| Ava | Aminovaleric acid |
| IMA | Nα-imidazole acetic acid |
| IMC | imidazole carboxylic acid |
| βAla | β-Alanine |

In one embodiment of the present invention, a group of preferred compounds includes:

γABUDTrpDTrpArgCOOH
α,γABUDTrpDTrpArgNH$_2$
α,γABUDTrpDTrpOrnNH$_2$
α,γABUDαNalDTrpLysNH$_2$
α,γABUDαNalDTrpArgNH$_2$
α,γAbuDαNalDTrpArgNH$_2$
αAibDTrpDTrpArgNH$_2$
αAibDαNalDTrpArgNH$_2$
αAibDTrpDTrpArgCOOH
αAibDαNalDTrpArgCOOH
αAibDαTrpDTrpArgNH$_2$

αAibDTrpDPheArgNH$_2$
inipDαNalDTrpPheNH$_2$
inipDαNalDTrpCHxAlaNH$_2$
inipDαNalDTrpPheCOOH
inipDαNalDTrpPalNH$_2$
inipDαNalDTrpThrNH$_2$
inipDαNalDTrpValNH$_2$
inipDαNalDβNalPheNH$_2$
inipDαNalDTrpPheCOOH
inipDβNalDTrpPheNH$_2$
α AibDTrpDProGlyNH$_2$
α AibDTrpDProPheNH$_2$
α AibDTrpDProProNH$_2$
αAibDTrpDProDProNH$_2$
αAibDTrpDProDPheNH$_2$
αAibDTrpDProDPalNH$_2$
αAibDTrpDProDTrpNH$_2$
αAibDTrpDProDLeuNH$_2$
αAibDTrpDProDHisNH$_2$
αAibDTrpDProDValNH$_2$
αAibDTrpDProGlnNH$_2$
αAibDTrpDProArgNH$_2$
αAibDTrpDProLysNH$_2$
αAibDTrpDProDAlaNH$_2$
inipDαNalDpClPhePheNH$_2$
inipDαNalDpClPheArgNH$_2$
inipDαNalDTrpDProNH$_2$
αAibDTrpDProDSerNH$_2$
αAibDTrpDProDThrNH$_2$ and
αAibDTrpDProDIleNH$_2$.

In another embodiment of the present invention, a group of preferred compounds includes:
inipDTrpDTrpPheLysNH$_2$
inipDβNalDTrpPheLysNH$_2$
γABUDβNalDTrpPheLysNH$_2$
α,γABUDTrpDTrpPheLysNH$_2$
βAlaDTrpDTrpPheLysNH$_2$
α,γABUDβNalDTrpPheLysNH$_2$
α,γABUDTrpDTrpPheArgNH$_2$
α,γABUDαNalDTrpPheArgNH$_2$
inipDβBNalDTrpPheLysNH$_2$
inipDTrpDTrpPheArgNH$_2$
βAlaDαNalDTrpPheArgNH$_2$
αAibDTrpDTrpPheArgNH$_2$
αAibDTrpDTrpPheArgCOOH
inipDTrpDTrpPheArgCOOH
inipDαNalDTrpPheArgNH$_2$
inipDαNalDTrpPheArgCOOH
inipDαNalDβNalPheArgNH$_2$
inipDαNalDTrpPheDSerNH$_2$
inipDαNalDTrpPheDThrNH$_2$
inipDαNalDTrpPheGlyNH$_2$
inipDαNalDTrpPheGlnNH$_2$
inipDαNalDTrpPheDGlnNH$_2$
αAibDαNalDTrpPheGlnNH$_2$
inipDαNalDTrpPheDHisNH$_2$
αAibDTrpDProPheArgNH$_2$
αAibDTrpDProPheDArgNH$_2$
αAibDTrpDProDValArgNH$_2$
αAibDTrpDProDValDLysNH$_2$
αAibDTrpDProDValDArgNH$_2$
αAibDTrpDProDProArgNH$_2$
αAibDTrpDProDProDPalNH$_2$
αAibDTrpDProDProDArgNH$_2$
αAibDTrpDProDIleDArgNH$_2$
αAibDTrpDProDIleArgNH$_2$
αAibDTrpDProDProDLysNH$_2$ and
αAibDTrpDProIleArgNH$_2$.

In the above Formula I, where X is $R_5$-$R_6$ and $R_6$ is a C(=O) (substituted heteroalicyclic or heteroaromatic), the heteroatom is selected from the group consisting of O, N, S and P.

The heteroalicyclic moiety preferably contains 2 to 12 carbon atoms, more preferably 3 to 8 carbon atoms. The heteroaromatic moiety preferably contains 5 to 12 carbon atoms, more preferably 5 to 11 carbon atoms. Substituents include NH$_2$, $C_1$–$C_{12}$ lower alkyl, and as listed below.

Examples include piperidine-3-methyl-benzylether, N-diethylnipectamide, N-piperazine methylsulfonamide, diethylamide, m-methylpiperidine, 3,3-diphenylpropylamide, 4-piperidino piperidinamide, 4-phenyl-piperidinamide, N-methyl 1-piperiazine, 2-morpholinoethylamine, spiroindole methylsulfonamide, pyrrolidine amide, indoleamide, 3-piperidine methanol amide, tropin amide, 2-aminoethylamide, 3-aminopropylamide, 4-aminobutylamide, 5-aminopentylamide, 6-aminohexylamide. Preferred substituted heteralicyclic or heteroaromatic include N-diethylnipectamide, piperidine-3-methyl-benzylether, N-piperazine methyl sulfonamide, diethylamide and m-methylpiperidine. Even more preferred are N-diethylnipectamide and piperidine-3-methyl-benzylether.

Preferably, the compound has the structure AibDTrpX, where X is DProNH$_2$, DPro-diisobutylamide, DProbutylamide, DPro-C(=O)(substituted heteroalicyclic or heteroaromatic), and DTrp-Phe-Arg-5-aminopentamide and organic and inorganic addition salts thereof. More preferably, X is DPro-diisobutylamide, DPro-C(=O) (substituted heteroalicyclic or heteroaromatic) and DTrp PheArg-5-aminopentamide, and organic and inorganic addition salts thereof. Still more preferably, X is DPro-diisobutylamide or DTrp-Phe-Arg-5-aminopentamide, and organic and inorganic addition salts thereof. Even more preferably, X is DPro-diisobutylamide and organic and inorganic addition salts thereof.

In an alternative embodiment the compound has the formula $$A_{1''}\text{-}Y,$$

wherein
$A_{1''}$ is Aib, inip, ABU, βAla, His, Sar or any of their respective D-isomers. The Aib residue can be substituted or unsubstituted. Preferred substituents include N- and N-,N-$C_1$–$C_6$ alkyl, halogens, N- and N-,N-2 hydroxyethyl, 3-hydroxypropyl, 4-hydroxybutyl and 3-hydroxyisobutyl. Aib is preferably unsubstituted. $A_{1''}$ is preferably Aib, inip or ABU. More preferably Aib is αAib. Abu is preferably γAbu or α,γAbu, more preferably α,γAbu.

Y is $A_{2'}$-$A_3$-$A_4$-$A_5$-$A_6$-Z',
$A_{2'}$-$A_3$-$A_4$-$A_5$-Z' or $A_{2'}$-$A_3$-$A_4$-Z'
wherein $A_{2'}$ is $A_5$-$A_{2''}$ or $A_{2''}$,
wherein $A_5$ is a spacer amino acid such as His,
$A_{2''}$ is as defined above for $A_2$. $A_{2''}$ is preferably DTrp, DαNal or DβNal. $A_{2''}$ is more preferably DTrp.
A3, A4 and A5 are any natural L-amino acid, Pal, αNal, βNal, Nle, Arg-DPro, DPCl, D or L (CHX), cyclohexylalanine (CHXAla), or any of their respective D-isomers, preferably $A_3$ is DPro, DTrp, DβNal or DPhe, more preferably $A_3$ is DPro or DTrp; and $A_4$ is preferably Gly, Phe, Pro, Ile, DPro, DPhe, DPal, DLeu, DHis, DVal, DGln, DIle, DNle, DArg, DAla, DSer, DThr, DIle, Arg, Orn Lys, Ala, Pal, Thr, Val, PheCHX, CHXAla or CHX. $A_4$ is preferably DSer, DAug, DPro, DTrp, DVal, DIle, DThr, DNVal, DNle, Ile, Pro, Phe and still more preferably, $A_4$ is DPro. $A_5$ is preferably Ile, Arg, Pal, DArg, DSer, Lys and Arg-DPro. More preferably $A_5$ is Arg, DArg, and Lys.

Z' is $NH_2$, OH or (aminoalkyl) or (aminoalkylamino), preferably the aminoalkyl is NH ($C_1$–$C_{10}$ alkyl) e.g. $NH(CH_2)_nCH_3$, where n is 1 to 10 such as

—N(H)(CH₂—CH₃);

N di-($C_1$–$C_{10}$ alkyl) e.g., N di-$(CH_2)_n$ $CH_3$ such as

—N(CH₂—CH₃)(CH₂—CH₃);

preferably the alkylamino is a NH ($C_1$–$C_{10}$ alkylamino, e.g. $NH(CH_2)_nNH_2$ such as

—N(H)(\);

N (di $C_1$–$C_{10}$ alkylamino), e.g., N [di-$(CH_2)_nNH_2$] such as

—N(CH₂—CH₂—NH₂)(CH₂—CH₂—NH₂).

Preferred examples include moieties such as -2-aminoethylamide, -3-aminopropylamide, -4-aminobutylamide, -5-aminopentylamide, or -6-aminohexylamide; N-dimethylamide; N-diethylamide; N-dipropylamide; N-dibutylamide; N-diisobutylamide; N-dipentylamide; N-dihexylamide;

A particularly preferred embodiment is Aib-Y, more preferably αAib-Y.

Y is preferably $A_{2''}$-DPro-$A_4$-$A_5$-$A_6$-Z'; $A_{2''}$-$A_3$-$A_4$-Z'; or $A_{2''}$-$A_3$-$A_4$-$A_5$Z'. Y is more preferably $A_{2''}$-DPro-$A_4$-Z' or $A_{2''}$-DPro-$A_4$-Z' or $A_{2''}$-DPro-$A_4$-$A_5$-Z'. Still more preferably Y is $A_{2''}$-DPro-$A_4$-$A_5$-Z'. Z' is preferably -$NH_2$.

Preferred embodiments include

αAib-DTrp-DPro-$A_4$-$A_5$-$A_6$-Z';
αAib-DTrp-DPro-$A_4$-$A_5$-Z';
αAib-DTrp-DPro-$A_4$-Z';
αAib-DTrp-DPro-$A_4$-Arg-$NH_2$;
αAib-DTrp-DPro-$A_4$-Arg-$A_6$-$NH_2$;
αAib-DTrp-DPro-$A_4$-Arg-Gly-$NH_2$;
αAib-DαNal-DPro-$A_4$-$A_5$-$A_6$-Z';
αAib-DαNal-DPro-$A_4$-$A_5$-Z';
αAib-DαNal-DPro-$A_4$-Z';'
αAib-DαNal-DPro-$A_4$-$NH_2$;
αAib-DαNal-DPro-$A_4$-Arg-$NH_2$;
and αAib-DαNal-DPro-$A_4$-Arg-Gly-$NH_2$.

$A_4$ is preferably DIle, DThr, DNle, DVal, DGln, DAla, DPhe, DTrp, DNVal and Arg.

Exemplery representatives of αAib-$A_{2''}$-DPro-$A_4$-Arg-Z' include

αAibDTrpDProDIleArg$NH_2$;
αAibDTrpDProDThrArg$NH_2$;
αAibDTrpDProDValArg$NH_2$;
αAibDTrpDProDNleArg$NH_2$; and
αAibDαNalDProDIleDArg$NH_2$.

Exemplary representatives of:

αAib-$A_{2''}$-DPro-$A_4$-Z include
αAib-DTrp-DPro-DThr-$NH_2$;
αAib-DTrp-DPro-DGln-$NH_2$;
αAib-DTrp-DPro-Arg-$NH_2$;
αAib-DTrp-DPro-DAla-$NH_2$;
αAib-DTrp-DPro-DPhe-$NH_2$;
αAib-DTrp-DPro-DTrp-$NH_2$;
αAib-DTrp-DPro-DVal-$NH_2$;
αAib-DTrp-DPro-DNVal-$NH_2$; and
αAib-DTrp-DPro-DIle-$NH_2$;

Exemplary representatives of αAib-$A_{2''}$-DPro-$A_4$-Arg-$A_6$-Z include compounds of the formula αAib-$A_{2''}$-DPro-$A_4$-Arg-Gly-$NH_2$ such as
αAib-DTrp-DPro-DIle-Arg-Gly-$NH_2$;
αAib-DTrp-DPro-DThr-Arg-Gly-$NH_2$; and
αAib-DTrp-DPro-DNle-Arg-Gly-$NH_2$.

Representative compounds are set forth below:

inipDαNalDTrp$NH_2$;
inipDαNalDVal$NH_2$;
αAibDTrpDVal$NH_2$;
αAibDTrpDProDSer$NH_2$;
αAibDTrpDProDArg$NH_2$;
αAibDTrpDProDPhe$NH_2$;
αAibDTrpDProDTrp$NH_2$;
αAibDTrpDValDVal$NH_2$;
αAibDValDProDVal$NH_2$;
αAibDValDValDVal$NH_2$;
αAibDTrpDProDLys$NH_2$;
αAibDProDProDVal$NH_2$;
inipDαNalDTrpDVal$NH_2$;
αAibDTrpDProIle$NH_2$;
αγAbuDαNalDTrpDIle$NH_2$;
inipDαNalDTrpDProIle$NH_2$;
inipDαNalDTrpPheIle$NH_2$;
inipDαNalDTrpDValArg$NH_2$;
αAibDTrpDProDValDVal$NH_2$;
αAibDTrpDProDProDPal$NH_2$;
αAibDTrpDProDValArgDPro$NH_2$;
αAibDTrpDProDIleDArg$NH_2$;
αγAbuDTrpDTrpDIle$NH_2$;
inipDαNalDTrpPheDVal$NH_2$;
αAibDTrpDProVal$NH_2$;
αAibDTrpDIleDIle$NH_2$;
αAibDTrpDProLeu$NH_2$;
αAibDTrpDProThr$NH_2$;
DHisDTrpDProDValArg$NH_2$;
DHisDTrpDProDThr$NH_2$;
αAibDTrpDProDIle$NH_2$;
αAibDTrpDPheDVal$NH_2$;
αAibDTrpDProDValDArg$NH_2$;
αAibDTrpDProDAla$NH_2$;
αAibDTrpDProDPro$NH_2$;
αAibDTrpDProArg$NH_2$;
αAibDTrpDProDVal$NH_2$;

inipDαNalDTrpDProNH$_2$;
αAibDαNalDProDValDArgNH$_2$;
αAlbDαNalDProDIleDArgNH$_2$;
αAibDTrpDProDProDLysNH$_2$;
αAibHisDαNalDPheLysNH$_2$;
αAibHisDTrpDProDValNH$_2$;
αAibHisDTrpDProDIleNH$_2$;
αAibHisDTrpDProValArgNH$_2$;
αAibHisDTrpDProDValArgNH$_2$;
αAibDαNalDProDValNH$_2$;
αAibDTrpDProDThrArgNH$_2$;
αAibDTrpDProDNleArgNH$_2$;
αAibDTrpDProDNValArgNH$_2$;
αAibDTrpDProIleArgNH$_2$;
αAibDTrpDProDProArgNH$_2$;
αAibDTrpDProProArgNH$_2$;
αAibDTrpDProDProDArgNH$_2$;
αAibDTrpDProDIleArgNH$_2$;
αAibDTrpDProPheDSerNH$_2$;
αAibDTrpDProPheArgNH$_2$;
αAibDTrpDProDValArgNH$_2$;
SarDTrpDTrpPheArgNH$_2$;
αAibDαNalDProDProArgNH$_2$;
αAibDαNalDProDNValArgNH$_2$;
αAibDαNalDProDIleArgNH$_2$;
αAibDαNalDProDValLysNH$_2$;
αAibDαNalDProDThrArgNH$_2$;
αAibDαNalDProDThrArgNH$_2$;
αAibDαNalDProDValArgNH$_2$;
αAibDαNalDProDValArgNH$_2$;
αAibDTrpDProDNleNH$_2$;
αAibDTrpDProDNValNH$_2$.
αAibDTrpDProDIle-X$_a$, where X$_a$ is
2-aminoethylamnide,
5-aminopentylamide, or
3-aminopropylamide.
αAibDTrpDProDVal-X$_b$, where X$_b$ is
2-aminoethylamide,
dimethylamide, or
diethylamide.
αAibDTrpDProDPro-X$_c$, where X$_c$ is
2-aminoethylamide.

The following compounds are preferred

αAibDTrpDProDIleXd, where X$_d$ is
5-aminopentylamide,
3-aminopropylamide,
2-aminoethylamide, or
4-aminobutylamide
αAibDTrpDProDValX$_e$, where X$_e$ is
N-dimethylamide,
N-diethylamide, or
2-aminoethylamide;
αAibDTrpDProDValX$_f$, where X$_f$ is
5-aminopentylamide;
αAibDTrpDProDNleX$_g$, where X$_g$ is
5-aminopentylamide;
αAibDTrpDProDProArgNH$_2$;
αAibDTrpDProDValDArgNH$_2$;
αAibDTrpDProDValArgNH$_2$;
αAibDTrpDProDIleArgNH$_2$;
αAibDαNalDProDValArgNH$_2$;
αAibDαNalDProDValArgNH$_2$;
αAibDαNalDProDIleArgNH$_2$;
αAibDαNalDProDValLysNH$_2$;
inipDαNalDαNalPheArgNH$_2$;
αAibDTrpDProDThrArgNH$_2$;
αAibDTrDProDNleArgNH$_2$;
αAibDTrpDProDNValArgNH$_2$;
αAibDTrpDProDIleArgGlyNH$_2$;
αAibDTrpDProDProDIleArgGlyNH$_2$;
αAibDTprDProDNleArgGlyNH$_2$; and
αAibDTrpDProDThrArgGlyNH$_2$;

In one embodiment one uses compound from compounds having the formula

αAibDTrpDProDProA$_4$ArgNH$_2$ or
αAibDTrpDProDProA$_4$ArgGlyNH$_2$.

Preferred examples are selected from the group consisting of

αAibDTrpDProDIleArgNH$_2$
αAibDTrpDProDIleArgGlyNH$_2$
αAibDTrpDProDProDIleArgNH$_2$, and
αAibDTrpDProDProDIleArgGlyNH$_2$.

In an alternate embodiment, the following peptides are of interest:

DβNalAlaTrpDPheLysGlnGlyNH$_2$
DAlaDTrpAlaTrpDPheLysValGlyNH$_2$
DAlaDβNalAlaTrpDPheLysGlnGlyGlyGlyNH$_2$
DAlaDTrpAlaTrpDPheLysHisGlyNH$_2$

These secretagogues can be used therapeutically for any use for which growth hormone can be used, such as treating hypothalamic pituitary dwarfism, osteoporosis, burns, and renal failure for acute use, for non-union bone fracture, and to promote wound healing. Additionally, it can be used to promote recovery from surgery, and acute/chronic debilitating medical illnesses. Beneficial anabolic effects result on skin, muscle and bone in relation to the aging process with a concomitant decrease in body fat. Treatment of cancer patients by these peptides is also included, for example, prevention and/or reduction of cachexia in cancer patients. These therapeutic uses are accomplished by using a therapeutically effective amount of the compound. Such an amount is that needed to promote the release of serum growth hormone levels as discussed, infra.

The compounds of this invention may also be used to enhance blood GH levels in animals; enhance milk production in cows; enhance body growth in animals such as, e.g., humans, sheep, bovines, and swine, as well as fish, fowl, other vertebrates and crustaceans; and increase wool and/or fur production in mammals. The amount of body growth is dependent upon the sex and age of the animal species, quantity and identity of the growth hormone releasing compound being administered, route of administration, and the like.

Also, the compounds of this invention increase serum GH in humans; enhance body growth in short stature children; decrease body fat and improve protein metabolism in select children; improve protein metabolism of the skin, muscle, bone while decreasing body fat of the elderly, particularly when GH deficiency is present.

These compounds are also useful for improving serum lipid pattern in humans by decreasing in the serum the amount of serum cholesterol and low density lipoprotein, and increasing in the serum the amount of the high density lipoprotein.

The novel secretagogues of this invention can be synthesized according to the usual methods of solution and solid phase peptide chemistry, or by classical methods known in the art.

In accordance with another embodiment of the present invention, a method is provided for promoting release and/or elevation of growth hormone levels in the blood of an animal. This method of promoting the release and/or elevation of growth hormone levels can also be used to therapeutically treat the aforesaid diseases. Said methods comprise administering to an animal an effective dose of at least one of the above-described compounds. In one embodiment, this method is used in animals other than humans.

The compounds of this invention can be administered by oral, parenteral (intramuscular (i.m.), intraperitoneal (i.p.), intravenous (i.v.) or subcutaneous (s.c.) injection), nasal, vaginal, rectal or sublingual routes of administration as well as intrapulmonary inhalation can be formulated in dose forms appropriate for each route of administration. Parenteral administration is preferred.

Solid dose forms for oral administration include capsules, tablets, pills, powders and granules. In such solid dose forms, the active compound is mixed with at least one inert carrier such as sucrose, lactose, or starch. Such dose forms can also comprise, as is normal practice, additional substances other than inert diluents, e.g., lubricating agents such as magnesium stearate. In the case of capsules, tablets and pills, the dose forms may also comprise buffering agents. Tablets and pills can additionally be prepared with enteric coatings.

Liquid dose forms for oral administration include emulsions, solutions, suspensions, syrups, the elixirs containing inert diluents commonly used in the art, such as water. Besides, such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dose forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in a medium of sterile water, or some other sterile injectable medium immediately before use.

The amount of secretagogues or combination of compounds of the present invention administered will vary depending on numerous factors, e.g., the particular animal treated, its age and sex, the desired therapeutic affect, the route of administration and which polypeptide or combination of polypeptides are employed. In all instances, however, a dose effective (therapeutically effective amount) to promote release and elevation of growth hormone level in the blood of the recipient animal is used. Ordinarily, this dose level falls in the range of between about 0.1 $\mu$g to 10 $\mu$g of total compound per kg of body weight. The preferred amount can readily be determined empirically by the skilled artisan based upon the present disclosure.

For example, in humans when the mode of administration is i.v. the preferred dose level falls in the range of about 0.1 $\mu$g to 10 $\mu$g of total secretagogue per kg of body weight, more preferably, about 0.5 $\mu$g to 5 $\mu$g of total secretagogue per kg of body weight, still more preferably about 0.7 $\mu$g about 3.0 $\mu$g per kg of body weight. When combinations of growth hormone releasing compounds are used, lower amounts of the presently described peptide can be used. For example, combining the presently described secretagogues with, for example, a synergistic compound in Group I of U.S. Pat. No. 4,880,778 such as GHRH, or U.S. Pat. Nos. 5,663,146 or 5,486,505, a preferred range is about 0.1 $\mu$g to about 5 $\mu$g of the presently described compound per kg of body weight and about 0.5 $\mu$g to about 15.04 $\mu$g of synergistic compound (e.g. GHRH) and more preferably about 0.1 $\mu$g to about 3 $\mu$g of the present compound with about 1.0 $\mu$g to about 3.0 $\mu$g of the synergistic compound per kg of body weight.

When the mode of administration is oral, greater amounts are typically needed. For example, in humans for oral administration, the dose level is typically about 30 $\mu$g to about 1200 $\mu$g of compound per kg of body weight, more preferably about 70 $\mu$g to about 600 $\mu$g of compound per kg of body weight, still more preferably, about 200 $\mu$g to about 600 $\mu$g of total compound per kg of body weight. Cows and pigs require about the same dose level as humans, while rats typically require higher dose levels. The exact level can readily be determined empirically based upon the present disclosure.

In general, as aforesaid, the administration of combinations of growth hormone releasing peptides will allow for lower doses of the individual growth hormone releasing compounds to be employed relative to the dose levels required for individual growth hormone releasing compounds in order to obtain a similar response, due to the synergistic effect of the combination.

Also included within the scope of the present invention are compositions that comprise, as an active ingredient, the organic and inorganic addition salts of the above-described polypeptides and combinations thereof; optionally, in association with a carrier, diluent, slow release matrix, or coating.

The organic or inorganic addition salts of the growth hormone releasing compounds and combinations thereof contemplated to be within the scope of the present invention include salts of such organic moieties as acetate, trifluoroacetate, oxalate, valerate, oleate, laurate, benzoate, lactate, tosylate, citrate, maleate, fumarate, succinate, tartrate, naphthalate, and the like; and such inorganic moieties as Group I (i.e., alkali metal salts), Group II (i.e. alkaline earth metal salts) ammonium and protamine salts, zinc, iron, and the like with counterions such as chloride, bromide, sulfate, phosphate and the like, as well as the organic moieties referred to above.

Pharmaceutically acceptable salts are preferred when administration to human subjects is contemplated. Such salts include the non-toxic alkali metal, alkaline earth metal and ammonium salts commonly used in the pharmaceutical industry including sodium, potassium, lithium, calcium, magnesium, barium, ammonium and protamine salts which are prepared by methods well known in the art. The term also includes non-toxic acid addition salts which are generally prepared by reacting the compounds of this invention with a suitable organic or inorganic acid. Representative salts include hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napthylate and the like.

The invention will be further illustrated by the following non-limiting examples.

EXAMPLES OF THE INVENTION

The following examples are designed to illustrate certain aspects of the present invention. The examples are not intended to be comprehensive of all features and all embodiments of the present invention, and should not be construed as limiting the claims presented herein.

General Methods for Synthesis

1H NMR spectra were measured ($SiMe_4$ internal standard) on a GE-500 (500 MHz) Spectrometer. Mass spectra data were obtained by using a "Lasermat" Laser Desorption Mass Spectrometry. Reagents were obtained from commercial sources and used without further purification. Solvents were dried according to standard procedures. Scheme 1 can be utilized for additions with any amine group recorded in Table 1.

Example 1

Synthesis of the Growth Hormone Releasing Peptides

Paramethyl benzhydrylamine hydrochloride (pMe-BHA HCl) resin is placed in a reaction vessel on a commercially available automated peptide synthesizer. The resin is substituted with free amine up to a loading of about 5 mmoles per gram. The compounds are prepared by coupling individual amino acids starting at the carboxy terminus of the peptide sequence using an appropriate activating agent, such as N,N' dicyclohexylcarbodiimide (DCC). The alpha amine of individual amino acids are protected, for example, as the t-butyloxycarbonyl derivative (t-Boc) and the reactive side chain functionalities are protected as outlined in Table 1.

TABLE 1

Side Chain Protecting Groups Suitable for Solid Phase Peptide Synthesis

| | |
|---|---|
| Arginine | $N^g$-Tosyl |
| Aspartic Acid | O-Benzyl |
| Cysteine | S-para-Methylbenzyl |
| Glutamic Acid | O-Benzyl |
| Histidine | $N^{im}$-Tosyl |
| Lysine | $N^\epsilon$-2, 4-Dichlorobenzyloxycarbonyl |
| Methionine | S-Sulfoxide |
| Serine | O-Benzyl |
| Threonine | O-Benzyl |
| Tryptophan | $N^{in}$-Formyl |
| Tyrosine | O-2, 6-Dichlorobenzyl |

Prior to incorporation of the initial amino acid, the resin is agitated three times (about one minute each) with dichloromethane ($CH_2C_{12}$: about 10 ml/gm of resin), neutralized with three agitations (about two minutes each) of N,N-diisopropylethylamine (DIEA) in dichloromethane (10:90; about 10 ml/gm of resin) and agitated three times (about one minute each) with dichloromethane (about 10 mL/gm of resin). The initial and each of the subsequent amino acids are coupled to the resin using a preformed symmetrical anhydride using about 6.0 times the total amount of the reaction capacity of the resin of a suitably protected amino acid and about 2.0 times the total amount of the binding capacity of the resin of DIC in an appropriate amount of dichloromethane. For amino acids with a low dichloromethane solubility, N,N-dimethylformamide (DMF) is added to achieve a homogenous solution. Generally, the symmetrical anhydride is prepared up to 30 minutes prior to introduction into the reaction vessel at room temperature or below. The dicyclohexylurea that forms upon preparation of the symmetrical anhydride is removed via gravity filtration of the solution into the reaction vessel. Progress of the coupling of the amino acid to the resin is commonly monitored via a color test using a reagent such as ninhydrin (which reacts with primary and secondary amines). Upon complete coupling of the protected amino acid to the resin (>99%), the alpha amine protecting group is removed by treatment with acidic reagent(s). A commonly used reagent consists of a solution of trifluororacetic acid (TFA) in dichloromethane (33:66).

After the desired amino acid sequence has been completed, the desired peptide can be cleaved from the resin support by treatment with a reagent such as hydrogen fluoride (HF) which not only cleaves the peptide from the resin, but also cleaves most commonly used side-chain protecting groups. When the BHA or p-Me-BHA resin is used, HF treatment results directly in free peptide amides. When an amino acid-Merrifield resin is used, free peptide alkylamides are cleaved by treatment with an appropriate amine (in this case, use of Boc-$N^\epsilon$-FMOC-Lys would allow simultaneous removal of the FMOC group).

The complete procedure for incorporation of each individual amino acid residue onto the resin is outlined in Table 2.

TABLE 2

Procedure for Incorporation of Individual Amino Acids onto a Resin

| | Reagent | Agitations | Time/Agitation |
|---|---|---|---|
| 1. | Dichloromethane | 3 | 1 min. |
| 2. | TFA-Dichloromethane (33:66) | 1 | 2 min. |
| 3 | TFA-Dichloromethane (33:66) | 1 | 20 min. |
| 4. | Dichloromethane | 3 | 1 min. |
| 5. | DIEA, DMF (10:90) | 2 | 2 min. |
| 6. | Dichloromethane | 3 | 1 min. |
| 7. | Boc amino acid/DIC | 1 | 15–120 min* |
| 8. | Dichloromethane | 3 | 1 min. |
| 10. | Monitor progress of the coupling reaction** | | |
| 11. | Repeat steps 1–12 for each individual amino acid | | |

*Coupling time depends upon the individual amino acid.
**The extent of coupling can be generally monitored by a color test. If the coupling is incomplete, the same amino acid can be recoupled by a different protocol, e.g. HOBt active ester. If the coupling is complete the next amino acid can then be coupled.

Using this procedure the compounds described in Tables 3, 4 and 5 were made.

Example 2

In Vivo GH Release in Rats

Immature female Sprague-Dawley rats were obtained from the Charles River Laboratories (Wilmington, Mass.). After arrival they were housed at 25° C. with a 14:10 hour light:dark cycle. Water and Purina rat chow were available ad libitum. Pups were kept with their mothers until 21 days of age.

Twenty-six day old rats, six rats per treatment group, were anesthetized interperitoneally with 50 mg/kg of pentobarbital 20 minutes prior to i.v. treatment with peptide. Normal saline with 0.1% gelatin was the vehicle for intravenous (i.v.) injections of the peptides. The anesthetized rats, weighing 55–65 grams, were injected i.v. with the quantity of grown hormone releasing compounds indicated in Table 3. Injection was made as a 0.1 mL solution into the jugular vein.

All animals were sacrificed by guillotine 10 minutes after final test injection (see Table 3). Trunk blood for the determination of blood GH levels was collected following decapitation. After allowing the blood to clot, it was centrifuged and the serum was separated from the clot. Serum was kept frozen until the day of sampling for radioimmunoassay (RIA) determination of growth hormone levels according to the following procedure, as developed by the National Institute of Arthritis, Diabetes and Digestive and Kidney Diseases (NIADDK).

Reagents are generally added to the RIA analysis tubes at a single sitting, at refrigerator temperature (about 4° C.) in the following sequence:

(a) buffer, (b) "cold" (i.e., non-radioactive) standard or unknown serum sample to be analyzed, (c) radio-iodinated growth hormone antigen, and (d) growth hormone antiserum.

Reagent addition is generally carried out so that there is achieved a final RIA tube dilution of about 1:30,000 (antiserum to total liquid volume; vol:vol).

The mixed reagents are then typically incubated at room temperature (about 25° C.) for about 24 hours prior to addition of a second antibody (e.g., goat or rabbit anti-monkey gamma globulin serum) which binds to and causes precipitation of the complexed growth hormone antiserum. Precipitated contents of the RIA tubes are then analyzed for the number of counts in a specified period of time in a gamma scintillation counter. A standard curve is prepared by plotting number of radioactive counts versus growth hormone (GH) level. GH levels of unknown are then determined by reference to the standard curve.

Serum GH was measured by RIA with reagents provided by the National Hormone and Pituitary Program.

Serum levels in Tables 3 and 4 are recorded in ng/mL in terms of the rat GH standard of 0.61 International Units/mg (IU/mg). Data is recorded as the mean ± standard error of the mean (SEM). Statistical analysis was performed with Student's t-test. In Table 3, the results shown are the average of studies with six rats.

Example 3

Synthesis of Aib-DTro-DPro-diisobutylamide (YL-156)

(1) Synthesis of DPro-Diisobutylamide (1)

1 mmol of Boc-DPro (Boc=tert-Butoxycarbonyl group) was dissolved in 30 ml dry $CH_2Cl_2$ in a 100 ml round bottom flask, with 1 mmol of 1-hydroxybenzotriazole added while stirring under $N_2$ atmosphere in an ice-bath, then 1.05 mmol of 1-ethyl-3-(3'-dimethylaminopropyl) carbodiimide HCl was added in 10 ml dry $CH_2Cl_2$ at a fast drop rate and the reaction mixture was stirred for 1 hour at 0° C. 1.1 mmol of diisobutylamine in 10 ml of $CH_2Cl_2$ was added dropwise and stirring was continued for a further 18 h at ambient temperature. The reaction mixture was washed with 20 ml of 20% aqueous citric acid, 20 ml of saturated aqueous $NaHCO_3$, and 20 ml of saturated aqueous sodium chloride. The organic layer was separated and dried over anhydrous magnesium sulfate, filtered and concentrated in vacuum. Further purification was done by flash column chromatography ($SiO_2$, $CHCl_3$/MeOH, 95:5) to afford white solid of Boc-DPro-diisobutylamide.

Under $N_2$ atmosphere, the Boc-DPro-diisobutylamide was dissolved in 25 ml of $CH_2Cl_2$ and 1-ml of trifluoracetic acid was added while being stirred. The reaction mixture was stirred for 30 min. Volatiles were removed under vacuum and the residue was dissolved in 30 ml of $CH_2Cl_2$ and washed with 10 ml saturated $NaHCO_3$ aqueous solution. The organic layer was removed and the aqueous layer was extracted with $CH_2Cl_2$ (3×10 ml). The organic layer was dried over anhydrous sodium sulfate and filtered and the solvent was removed in vacuum. The residue was further purified by column chromatography ($SiO_2$, $CHCl_3$/MeOH, 85:15) to afford 0.73 mmol (73%) of compound (1) which was characterized by TLC on mass spectra, $M^+$=225.1.

(2) Synthesis of DTrp-DPro-diisobutylamide (2)

In a 100 ml round bottom flask, 0.70 mmol of Boc-DTrp was dissolved in 25 ml dry $CH_2Cl_2$ and 0.70 mmol of 1-hydroxybenzotriazole was added while stirring under $N_2$ atmosphere in an ice-bath then 0.75 mmol of 1-ethyl-3-(3'-dimethylaminopropyl) carbodiimide HCl was added in 15 ml dry $CH_2Cl_2$ at a fast drop rate and the reaction mixture stirred for 1 hour at 0° C. 0.71 mmol of (1) in 20 ml of $CH_2Cl_2$ was added dropwise and stirring was continued for a further 18 h at ambient temperature. The reaction mixture was washed with 20 ml of 20% citric acid aqueous solution, 20 ml of saturated $NaHCO_3$ aqueous solution, and 20 ml of saturated sodium chloride aqueous solution. The organic layer was separated and dried over anhydrous magnesium sulfate, filters and concentrated by vacuum. Further purification was done by flash column chromatography ($CHCl_3$/MeOH, 95:5) to afford white solid of Boc-DTrp-D-diisobutylamide.

Under $N_2$ atmosphere, the Boc-DTrp-DPro-diisobutylamide was dissolved in 25 ml of $CH_2Cl_2$, 1 ml of methylsulfide and 0.5 ml of 1,2-ethanedithiol was added as scavenger in suppressing the indole alkylation of tryptophane. 10 ml of trifluoracetic acid was added dropwise while being stirred. The reaction mixture was stirred for 30 min. Volatiles were removed under vacuum and the residue was dissolved in 30 ml of $CH_2Cl_2$ and washed with 10 ml saturated $NaHCO_3$ aqueous solution. The organic layer was dried over anhydrous sodium sulfate and filtered and the solvents were removed in vacuum. The residue was further purified by column chromatography ($SiO_2$, $CHCl_3$/MeOH, 85:15) to afford 0.55 mmol (78.5%) of compound (2) which was characterized by TLC and mass spectra, $M^+$=411.5.

(3) Synthesis of Aib-DTrp-DPro-diisobutylamide (YL-156)

In a 100 ml round bottom flask, 0.50 mmol of Boc-Aib (Aib=α-aminoisobutyric acid) was dissolved in 30 ml dry $CH_2Cl_2$ and then 0.51 mmol of 1-hydroxybenzotrizole was added while stirring under $N_2$ atmosphere in an ice-bath, 0.55 mmol of 1-ethyl-3-(3'-dimethylaminopropyl) carbodiimide HCl was added in 20 ml dry $CH_2Cl_2$ at a fast drop rate and the reaction was stirred for 1 hour at 0° C. 0.51 mmol of (2) in 15 ml of $CH_2Cl_2$ was added dropwise and stirring was continued for a further 18 h at ambient temperature. The reaction mixture was washed with 20 ml of 20% citric acid aqueous solution, 20 ml of saturated $NaCHO_3$ aqueous solution, and 20 ml of saturated sodium chloride aqueous solution. The organic layer was separated and dried over anhydrous magnesium sulfate, filtered and concentrated in vacuum. Further purification was done by flash column chromatography ($CHCl_3$/MeOH, 95:5) to afford white solid of Boc-Aib-DTrp-DPro-diisobutylamide.

Under $N_2$ atmosphere, the Boc-Aib-DTrp-DPro-diisobutylamide was dissolved in 30 ml of $CH_2Cl_2$, 1 ml of methylsulfide and 0.5 ml of 1,2-ethanedithiol were added as scavengers to suppress the indole alkylation of tryptophan. 10 ml of trifluoracetic acid was added dropwise while being stirred. The reaction mixture was stirred for 30 min. Volatiles were removed under vacuum and the residue was dissolved in 30 ml of $CH_2Cl_2$ and washed with 10 ml saturated $NaHCO_3$ aqueous solution. The organic layer was removed and the aqueous layer was extracted with $CH_2Cl_2$ (3×10 ml). The organic layer was dried over anhydrous sodium sulfate, and filtered and the solvents were removed in vacuum. The residue was further purified by column chromatography (SiO$_2$, CHCl$_3$/MeOH, 85:15) to afford 0.43 mmol (86.2%) of compound (YL-156) which was characterized by TLC and mass spectra M$^+$=497.6.

Example 4

Synthesis of inip-DαNal-DTrp-Phe-2-aminoethylamide (YL-105)

3.5 g of Wang resin with the peptide attached was supplied by Research Genetics Laboratory. It was added to a 100 ml round-bottom flask and then sequentially 40 ml of dry CH$_2$C$_2$, 4 ml of methanol and 2 ml of 1,2-diaminoethane were added while stirring under N$_2$ atmosphere. The reaction mixture was stirred for 72 hours at RT. The reaction mixture was filtered and the resin was washed with 20 ml of dry CH$_2$Cl$_2$, 20 ml of methanol. The solid resin was discarded. The organic solvent was removed by vacuum. The solid residue was further purified by flash column chromatography (SiO$_2$, CHCl$_3$/MeOH, 95:5) to afford white solid of YL-105.

Further purification was performed by preparative HPLC. Molecular weight was determined by MS.

Example 5

Synthesis of (N-2-hydroxylethyl-Aib-DTrp-DPro-diisobutylamide (YL-185)

Reductive Alkylation 1 mmol of YL-156 (αAibDTrpDPro-diisobutylamide)was dissolved in 40 ml dry methanol in a 100 ml round-bottom flask and 1.5 mmol of NaBH$_4$ in THF was added while stirring under N$_2$ atmosphere. The solution was acidified by adding trifluoracetic acid in methanol to adjust the pH to 6.5. Then 1.15 mmol of ethylaldehyde was added in 10 ml dry methanol and the reaction mixture was stirred for 16 hours at RT. The solvent was removed by vacuum. The remaining residue was dissolved in 30 ml CH$_2$Cl$_2$ and washed with 20 ml of saturated aqueous NaHCO$_3$. The organic layer was separated and dried over anhydrous magnesium sulfate, filtered, and concentrated in vacuum. Further purification was done by flash column chromatography (SiO$_2$,CHCl$_3$/MeOH, 95:5) to afford white solid of YL-185.

Further purification was performed by preparative HPLC. The molecular weight was determined by MS.

Example 6

Synthesis of (N-isobutyl)Aib-DTrp-DPro-diisobutylamide (YL-194)

Hoffman Alkylation 1 mmol of YL-156 (αAibDTrpDPro-diisobutylamide) was dissolved in 40 ml dry CH$_2$Cl$_2$ in a 100 ml round-bottom flask. 2 mmol of K$_2$CO$_3$ was then added while stirring under N$_2$ atmosphere. 1.15 mmol of 1-bromo-2-methylpropane was added in 10 ml dry CH$_2$Cl$_2$ and the reaction mixture stirred for 72 hours at RT. The reaction mixture was washed with 20 ml of saturated aqueous NaHCO$_3$ and 20 ml of saturated aqueous sodium chloride. The organic layer was separated and dried over anhydrous magnesium sulfate, filtered and concentrated under vacuum. Further purification was done by flash column chromatography (SiO$_2$, CHCl$_3$/MeOH, 95:5) to afford white solid of YL-194.

Further purification was performed by preparative HPLC. Molecular weight was determined by MS.

Example 7

Synthesis of Aib-DTrp-DTrp-Phe-Arg-5-aminopentylamide (YL-174)

0.7 mmol of Fmoc-Aib-DTrp-DTrp-Phe-ArgCOOH was synthesized by Research Genetics Laboratory by the solid phase method and added to a 100 ml round-bottom flask with 40 ml of dry CH$_2$Cl$_2$. 0.70 mmol of 1-hydroxybenzotriazole was added while stirring under N$_2$ atmosphere in an ice-bath and subsequently 0.75 mmol of 1-ethyl-3-(3'-dimethylaminopropyl)carbodiimide HCl was added in 15 ml dry CH$_2$Cl$_2$ at a fast drop rate. The reaction mixture was stirred for 1 hour at 0° C. 10 mmol of 1,5-diaminopentane in 20 ml of CH$_2$Cl$_2$ was added quickly and stirring was continued for an additional 18 h at ambient temperature. The reaction mixture was washed with 20 ml of saturated NaHCO$_3$ aqueous solution and 10 ml of saturated sodium chloride aqueous solution. The organic layer was separated and dried over anhydrous magnesium sulfate, filtered and concentrated under vacuum. Further purification was done by flash column chromatography (CHCl$_3$/MeOH, 95:5) to afford white solid of Fmoc-Aib-DTrp-DTrp-Phen-ArgCONH(CH$_2$)$_5$NH$_2$. This compound was dissolved in 20 ml of CH$_2$Cl$_2$ and under N$_2$ atmosphere 10 ml of piperidine was added. The solution was stirred for another 4 hours. The solvent was removed by vacuum and the residue was further purified by flash column chromatography (CHCl$_3$/MeOH, 95:5) to afford white solid of YL-174.

Further purification was performed by preparative HPLC. Molecular weight was determined by MS.

Example 8

Synthesis of Aib-DTrp-DPro-3-methylpiperidinamide (YL-111)

(Aib-DTrp-DPro-R, R=various of amine end groups, for example piperidine, 3-methyl piperidine, etc. All other Aib-DTrp-DPro-R compounds can be synthesized by using the same procedure):
(1) Synthesis of DPro-3-methylpiperidinamide (methylpiperidine) (1)

1 mmol of Boc-DPro (Boc=tert-Butoxycarbonyl group) was dissolved in 30 ml dry CH$_2$Cl$_2$ in a 100 ml round-bottom flask, 1 mmol of 1-hydroxybenzotriozole added while stirring under N$_2$ atmosphere in an ice-bath, 1.05 mmol of 1-ethyl-3-(3'-dimethylaminopropyl) carbodiimide HCL was added in 10 ml dry CH$_2$Cl$_2$ at a fast drop rate and the reaction mixture stirred for 1 hour at 0° C. 1.1 mmol of 3-methylpiperazine in 10 ml of CH$_2$Cl$_2$ was added dropwise and stirring was continued for an additional 18 h at ambient temperature. The reaction mixture was washed with 30 ml of 20% aqueous citric acid, 30 ml of saturated aqueous NaHCO$_3$, and 30 ml of saturated aqueous sodium chloride. The organic layer was separated and dried over anhydrous magnesium sulfate, filtered, and concentrated in vacuum. Further purification was done by flash column chromatography (SiO$_2$, CHCl$_3$/MeOH, 95:5) to afford white solid of Boc-DPro-D-piperidinamide.

Under N$_2$ atmosphere, the Boc-DPro-3-piperidinamide was dissolved in 25 ml of CH$_2$Cl$_2$ and 10 ml of trifluoracetic acid added while stirring. The reaction mixture was stirred for 30 min. All volatiles were removed under vacuum and the residue dissolved in 30 ml of CH$_2$Cl$_2$ and washed with 10 ml saturated $NaHCO_3$ aqueous solution. The organic layer was removed and the aqueous layer extracted with $CH_2Cl_2$ (3×10 ml). The organic layer was dried over anhydrous sodium sulfate and filtered and the solvent was removed by vacuum. The residue was further purified by column chromatography ($SiO_2$, $CHCl_3$/MeOH, 85:15) to afford 0.65 mmol (65%) of compound (1) which was characterized by TLC and mass spectra, $M^+$=196.3.

(2) Synthesis of DTrp-DPro-3-methylpiperidinamide (methylpiperidine) (2)

In a 100 ml round-bottom flask, 0.63 mmol of Boc-DTrp was dissolved in 25 ml dry $CH_2Cl_2$ 0.66 mmol of 1-hydroxybenzotrizole was added while stirring under N2 atmosphere in an ice-bath. 0.63 mmol of 1-ethyl-3-(3'-dimethylaminopropyl) carbodiimide HCL was added in 10 ml dry $CH_2Cl_2$ at a fast drop rate and the reaction mixture was washed with 20 ml of 20% citric acid aqueous solution, 20 ml of saturated $NaHCO_3$ aqueous solution and 20 ml of saturated sodium chloride aqueous solution. The organic layer was separated and dried over anhydrous magnesium sulfate, filtered and concentrated in vacuum. Further purification was done by flash column chromatography ($CHCl_3$/MeOH, 95:5) to afford white solid of Boc-DTrp-DPro-3-piperidinamide.

Under $N_2$ atmosphere, the Boc-DTrp-DPro-3-piperidinamide was dissolved in 25 ml of $CH_2Cl_2$ and 10 ml of trifluoracetic was added while being stirred. The reaction mixture was stirred for 30 min. All volatiles were removed under vacuum and the residue was dissolved in 30 ml of $CH_2Cl_2$ and washed with 10 ml saturated $NaHCO_3$ aqueous solution. The organic layer was removed and the aqueous layer was extracted with $CH_2Cl_2$ (3×20 ml). The organic layer was dried over anhydrous sodium sulfate, filtered and the solvent removed in vacuum. The residue was further purified by column chromatography ($SiO_2$, $CHCl_3$/MeOH, 85:15) to afford 0.43 mmol (68.3%) of compound (2) which was characterized by TLC and mass spectra, $M^+$=382.46.

(3) Synthesis of Aib-DTrp-DPro-3-methylpiperidinamide (methylpiperidine) (YL-111)

In a 50 ml round bottom flask, 0.33 mmol of Boc-Aib was dissolved in 20 ml dry $CH_2Cl_2$ and then 0.31 mmol of 1-hydroxybenzotriazole was added while stirring under $N_2$ atmosphere in an ice-bath. 0.35 mmol of 1-ethyl-3-(3'-dimethylaminopropyl)carbodiimide HCL was added in 10 ml dry $CH_2Cl_2$ at a fast drop rate and the reaction mixture was stirred for 1 hour at 0° C. 0.30 mmol of (2) in 15 ml of $CH_2Cl_2$ was added dropwise and stirring was continued for an additional 18 h at ambient temperature. The reaction mixture was washed with 20 ml of 20% citric acid aqueous solution, 20 ml of saturated $NaHCO_3$ aqueous solution and 20 ml of saturated sodium chloride aqueous solution. The organic layer was separated and dried over anhydrous magnesium sulfate, filtered and concentrated in vacuum. Further purification was done by flash column chromatography ($CHCl_3$/MeOH, 95:5) to afford white solid of Boc-Aib-DTrp-DPro-3-piperidinamide.

Under $N_2$ atmosphere, the Boc-Aib-DTrp-DPro-3-piperidinamide was dissolved in 25 ml of $CH_2Cl_2$ and 10 ml of trifluoracetic acid was added while being stirred. The reaction mixture was stirred for 30 min. All volatiles were removed under vacuum and the residue was dissolved in 30 ml of $CH_2Cl_2$ and washed with 10 ml saturated $NaCHO_3$ aqueous solution. The organic layer was removed and the aqueous layer was extracted with $CH_2Cl_2$ (3×10 ml). The organic layer was dried over anhydrous sodium sulfate, filtered and the solvent removed in vacuum. The residue was further purified by column chromatography ($SiO_2$, $CHCl_3$/MeOH, 85:15) to afford 0.28 mmol (84.8%) of compound (YL-111) which was characterized by TLC and mass spectra $M^+$=468.6.

Biological Activity

In vitro and in vivo activity of certain compounds were determined in rats and adult beagle dogs (in vivo activity only). The results are described in Tables 3, 4, 5, 6 and 7 below.

The GHRP-2 (reference standard) has the structure DAla-DβNal-Ala-Trp-DPhe-Lys-$NH_2$ (Chen and Clarke, *J. Neuroend.* 7: 179 (1995)).

TABLE 3

In Vitro Release of Growth Hormone in Rat

| Compound $R^1$-$N_2$-Aib DTrpX* Where X is: | control | GHRP-2 .001 | .0001 | .0003 | .001 | .003 | .01 | .03 | .1 | .3 | GH ng/ml 1 |
|---|---|---|---|---|---|---|---|---|---|---|---|
| DPrO $NH_2$ | 752 | 1525 | 922 | 1102 | 997 | 1250 | 1535 | 1550 | 1716 | | |
| DPro-diisobutylamide | 523 | 1307 | | | | | 1322 | 1529 | 1427 | 1155 | 1124 |
| $R^1$ = N-2-Ohethyl DPro-diisobutylamide | 341 | 1427 | — | — | 452 | 326 | 526 | 820 | 1163 | 1217 | |
| $R^1$ = $N_2$N-di-2-OHethyl/ DPro diisobutylamide | 341 | 1427 | — | — | 433 | 395 | 446 | 592 | 905 | 1206 | |
| $R^1$ = N-ethyl/DPro diisobutylamide | 510 | 1413 | — | — | 523 | 461 | 779 | 742 | 1079 | 1292 | |
| $R^1$ = Nentyl/ DPro diisobutylamide | 341 | 1427 | — | — | 570 | 698 | 982 | 1307 | 1467 | 1387 | |
| DPro- | 543 | 1065 | 554 | 578 | 554 | 630 | 823 | 908 | 925 | | |

TABLE 3-continued

In Vitro Release of Growth Hormone in Rat

| Compound R¹-N₂-Aib DTrpX* Where X is: | control | GHRP-2 .001 | .0001 | .0003 | .001 | .003 | .01 | .03 | .1 | .3 | GH ng/ml 1 |
|---|---|---|---|---|---|---|---|---|---|---|---|
| dipropylamide DPro-butylamide | 523 | 1307 | 512 | 647 | 833 | 995 | 1253 | 1612 | | | |
| DPro-pentylamide | 622 | 1290 | | | 569 | 830 | 1172 | 1184 | 1335 | 1451 | |
| DPro-dipentylamide | 523 | 1307 | | | 1348 | 1561 | 1287 | 1021 | 1451 | | |
| DPro-piperidine-3-methylbenzyl ether | 389 | 821 | 529 | 553 | 721 | 728 | 886 | 978 | | | |
| N,N-diethylnipecotamide | 397 | 593 | 418 | 395 | 489 | 536 | 642 | | | | |
| -N-piperazine methylsulfonamide | 553 | 1167 | | 672 | 675 | 856 | 1049 | | | | |
| DPro-diethylamide | 389 | 821 | 375 | 368 | 481 | 587 | 802 | 912 | | | |
| DPro-m-methylpiperidine | 308 | 1052 | 434 | 458 | 633 | 837 | 968 | | | | |
| DPro-3,3-diphenylpropylamide | 466 | 1126 | | | 926 | 1118 | 1169 | 1177 | 1283 | | |
| DPro-4-piperidinopiperidinamide | 376 | 1125 | | 419 | 451 | 540 | 808 | | | | |
| DPro-4-phenylpiperidinamide | 455 | 1520 | 624 | 777 | 1034 | 1186 | 1533 | 1772 | | | |
| DPro-N-methylpiperiazine | 389 | 821 | 467 | 532 | 573 | 605 | 816 | 909 | | | |
| DPro-2-morpholinoethylamine | 397 | 593 | 394 | 413 | 433 | 485 | 548 | | | | |
| DPro-spiroindole methylsulfonamide | 385 | 915 | 440 | 512 | 691 | 819 | 956 | 922 | 1057 | | |
| DPro-pyrrolidine amide | 614 | 1288 | 714 | 873 | 1149 | 1241 | | | | | |
| DPro-indoline amide | 486 | 1344 | | | 836 | 1127 | 1283 | 1235 | 1258 | 1220 | 1327 |
| DPro-3-piperidine methanol amide | 486 | 1344 | | | 1008 | 1199 | 1209 | 1348 | 1626 | 1567 | |
| DPro-tropin amide | 510 | 1220 | | | 542 | 797 | 1001 | 1124 | 1234 | | |
| DTrpPhe-Arg-5-amino pentamide | 752 | 1525 | 1228 | 1416 | 1712 | 1648 | 1621 | | | | |

*Unless otherwise stated, R¹ is H

TABLE 4

In Vivo Release of Growth Hormone in Rat

| Compound R$^1$-N$_2$-AibDTrpX* Where X is: | control | GHRP-2 .1 | .1 | .3 | 1 | 3 | 10 | 30 | GH ng/ml 100 |
|---|---|---|---|---|---|---|---|---|---|
| DPro NH$_2$ | 223 | 1580 | 326 | 433 | 1159 | 2217 | 3155 | | |
| DPro-diisobutylamide | 111 | 1066 | | | 642 | 1524 | 1837 | 2307 | 2913 |
| R$^1$ = N-2-OHethyl/ DPro-diiso-butylamide | 92 | 2051 | — | — | — | 156 | 259 | 451 | — |
| R$^1$ = N,N-di-2-OHethyl/ DPro-diiso-butylamide | 96 | 799 | — | — | — | | 124 | 208 | 543 |
| R$^1$ = N-ethyl/ DPro-diiso-butylamide | 92 | 2051 | — | — | 189 | 177 | 268 | 374 | — |
| R$^1$ = N-pentyl/ DPro-diiso-butylamide | 92 | 2051 | — | — | 124 | 398 | 371 | 789 | — |
| DPro-dipropylamide | 91 | 1082 | 92 | 220 | 305 | 579 | 1646 | 2089 | |
| DPro-butylamide | 111 | 1066 | | | 196 | 329 | 647 | 2005 | 1596 |
| DPro-pentylamide | 170 | 1289 | | | 310 | 581 | 820 | 1660 | 2280 |
| DPro-dipentylamide | 128 | 1071 | 87 | 182 | 322 | 355 | 632 | 482 | 1206 |
| DPro-piperidine-3-methyl-benzyl ether | 150 | 1235 | | | 669 | 1725 | 2319 | | |
| N,N-diethylnipecot-amide | 117 | 579 | | 221 | 928 | 2070 | 2896 | 2186 | |
| -N-piperazine methyl-sulfonamide | 113 | 942 | | 241 | 933 | 1965 | 1997 | | |
| DPro-diethylamide | 128 | 919 | | | 448 | 766 | 1719 | 2465 | 3088 |
| DPro-m-methylpiperidine | 93 | 445 | | | | 832 | 1557 | 1570 | 1762 |
| DPro-3,3-diphenyl-propylamide | 114 | 1106 | 141 | 147 | 138 | 249 | 383 | 624 | |
| DPro-4-piperidino-piperidin-amide | 150 | 1235 | | | | 378 | 1318 | 2403 | |
| DPro-4-phenylpiperidin-amide | 111 | 568 | | 112 | | 238 | | 499 | |
| DPro-N-methyl-piperazine | 128 | 919 | 218 | 425 | 1974 | 2314 | | | |
| DPro-2-morpholino-ethylamine | 111 | 568 | | | | 900 | 1585 | 2195 | |
| DPro-spiroindole methyl-sulfonamide | 120 | 586 | | | | 192 | 485 | 861 | 1177 |
| DPro-pyrrolidine amide | 98 | 1227 | | | | 1024 | 2116 | 2381 | |
| DPro-indoline amide | 69 | 1279 | | | 142 | 317 | 269 | 885 | |
| DPro-3-piperidine methanol amide | 91 | 1082 | 155 | 668 | 1483 | 2616 | 2711 | | |
| DPro-tropin amide | 73 | 1814 | | 114 | 87 | 183 | 362 | 383 | 769 |
| DTrpPhe-Arg-5-amino pentamide | 109 | 1718 | 2628 | 2740 | 2272 | 2929 | | | |

*Unless otherwise stated, R$^1$ is H

TABLE 5

In Vivo Release of Growth Hormone in Adult Beagle Dogs

| Compound R$^1$-N$_2$-AibDTrpX* Where X is: | oral dose (mg/kg) | 0 | 0.5 | 1 | 2 | 3 | 4 | 5 | 6 | 7 | Time (hr) 8 |
|---|---|---|---|---|---|---|---|---|---|---|---|
| DPro NH$_2$ | 4 | 0.7 | 38 | 14 | 9.5 | 13 | 7.1 | 3.3 | 4 | 2.5 | 1.3 |
| | 4 | 0.8 | 54 | 30 | 15 | 12 | 4.8 | 4.2 | 3.4 | 1 | 0.8 |
| DPro-diisobutylamide | 4 | 0.8 | 27 | 9.4 | 14 | 22 | 22 | 21 | 11 | 6.9 | 5.4 |
| | 4 | 1.4 | 141 | 50 | 74 | 15 | 7.5 | 4 | 4.4 | 5.7 | 2.3 |
| | 2 | 0.6 | 54 | 30 | 22 | 15 | 7 | 4.6 | 4.8 | 2.7 | 1.8 |
| | 1 | 2.6 | 85 | 30 | 16 | 7.7 | 6 | 0.9 | 2.5 | 2.5 | 1.6 |
| | 1 | <0.5 | 128 | 50 | 24 | 24 | 5.6 | 6.1 | 2.9 | 2.2 | — |
| | 1 | 1.5 | 89 | 59 | 30 | 11 | 7 | 6.2 | 5.2 | 3.7 | 3.2 |
| R$^1$ = N-2-OHethyl/ | 1 | 3.8 | 102 | 26 | 25 | 10 | 6.1 | 5.6 | 4.0 | 5.2 | 5.0 |

TABLE 5-continued

In Vivo Release of Growth Hormone in Adult Beagle Dogs

| Compound R$^1$-N$_2$-AibDTrpX* Where X is: | oral dose (mg/kg) | 0 | 0.5 | 1 | 2 | 3 | 4 | 5 | 6 | 7 | Time (hr) 8 |
|---|---|---|---|---|---|---|---|---|---|---|---|
| DPro-diisobutyl-amide | 1 | 1 | 62 | 30 | 19 | 5.6 | 3.8 | 2.0 | 2.5 | 2.0 | 1.6 |
| R$^1$ = N$_2$N-di-2-OHethyl/DPro-diisobutylamide | 1 | | | | | | | | | | |
| R$^1$ = N-ethyl/DPro-diisobutyl-amide | 4 | 1.3 | 100 | 29 | 20 | 9.4 | 3.9 | 2.2 | 2.4 | 1.5 | 5.6 |
| | 1 | 1.1 | 17 | 4.4 | 1.2 | 1.5 | 1.4 | 1.1 | 1.2 | 1.4 | 1.2 |
| R$^1$ = N-pentyl/DPro-diisobutyl-amide | 1 | | | | | | | | | | |
| DPro-dipropylamide | 4 | 3.2 | 112 | 52 | 29 | 25 | 13 | 6.1 | 3.6 | 2.9 | 2.5 |
| | 1 | 0.6 | 27 | 19 | 5.6 | 1.6 | 1.6 | 0.6 | 1.4 | 0.8 | 0.8 |
| DPro-butylamide | 4 | 1.1 | 92 | 43 | 26 | 53 | 14 | 5.4 | 3.5 | 3.9 | 1.3 |
| | 2 | 1.8 | 60 | 40 | 13 | 3.8 | 3.7 | 2.2 | 2.6 | 2.4 | 1.7 |
| DPro-pentylamide | 4 | 1 | 72 | 12 | 11 | 6 | 4.9 | 3.5 | 2.5 | 1.9 | 1.4 |
| DPro-dipentylamide | 4 | 2.3 | 53 | 20 | 1.3 | 15 | 15 | 8.9 | 9.2 | 6.6 | 4.3 |
| | 4 | 3.7 | 32 | 11 | 8.4 | 7.2 | 3.6 | 3.5 | 2.3 | 2.7 | <0.1 |
| | 4 | 2.9 | 11 | 11 | 15 | 3 | 3.3 | 2.5 | 2.7 | 2.3 | 2 |
| DPro-piperidine-3-methyl-benzyl ether | 4 | 2 | >128 | 59 | 63 | 28 | 11 | 6.7 | 4.2 | 4.1 | 1.8 |
| | 4 | 0.8 | 127 | 28 | 27 | 11 | 14 | 14 | 11 | 4.7 | 6.8 |
| | 2 | 3.2 | 169 | 42 | 63 | 45 | 13 | 5.5 | 4.5 | 3.4 | 3.2 |
| | 2 | 3.6 | 112 | 39 | 23 | 6.3 | 4.5 | 1.7 | 2.7 | 2.3 | 1.9 |
| | F0.5iv | 2.9 | 81 | 78 | 27 | 9.3 | 4.5 | 4.1 | 2.9 | 4.1 | 4.1 |
| N,N-diethylnipe-cotamide | 4 | 1.7 | 57 | 13.8 | 5.3 | 5.5 | 3.4 | 3.1 | 1.9 | 2 | 1.7 |
| | 4 | 0.9 | 43 | 7.3 | 2 | 2.1 | 0.8 | 0.9 | 2.1 | 6.9 | 0.9 |
| | 4F | 2.7 | 6.3 | 3.5 | 3.7 | 2.2 | 0.9 | 10.1 | 3.6 | 3.5 | 3.5 |
| -N-piperazine methyl-sulfonamide | 4 | 2.1 | 57 | 12.5 | 8.7 | 3.8 | 1.7 | 2.2 | 1.6 | 6.3 | 3.2 |
| DPro-diethylamide | 4 | 2.4 | 56 | 38 | 29 | 28 | 16 | 9.1 | 6.2 | 3.9 | 2.8 |
| | 4 | 1.7 | 134 | 89 | 105 | 86 | 16 | 7.1 | 5.1 | 4.5 | 3.2 |
| | F0.5iv | 1.6 | 60 | 18 | 6 | 3.7 | 2.5 | 2 | 1.9 | 1.7 | 2.5 |
| DPro-m-methylpiperidine | 4 | 1 | 54 | — | 50 | 52 | 20 | 27 | 8.1 | 9.6 | 1.7 |
| | 4F | 1.4 | 72 | 84 | 18 | 4.7 | 3.5 | 1.4 | 1.1 | 1.6 | 1.5 |
| | 4 | 2.1 | 118 | 55 | 54 | 53 | 34 | 13 | 11 | 11 | 6.4 |
| | 2 | 1.2 | 128 | 59 | 29 | 12 | 8.9 | 3.6 | 3 | 3 | 1.7 |
| | 1 | 1.6 | 53 | 19 | 15 | 9.6 | 3.1 | 2.2 | 1.5 | 2.2 | 1 |
| | 1 | 2 | 63 | 32 | 17 | 13 | 12 | 1.5 | 2.4 | 3 | 2.2 |
| DPro-3,3-diphenyl-propylamide | 4 | 1.6 | 119 | 54 | 17 | 16 | 10 | 5.6 | 4.2 | 3.3 | 2.7 |
| | 4 | 2.2 | 54 | 12 | 8.6 | 7.4 | 13 | 5.9 | 3.4 | 3 | ns |
| DPro-N-methyl-1-piperazine | 4 | 1 | 100 | 22 | 8.3 | 7.9 | 4.8 | 2.6 | 2.9 | 2.3 | 1.8 |
| | 0.5iv | 0.8 | 41 | 31 | 7 | 3.3 | 2.6 | 1.5 | 2.4 | 0.9 | 1.1 |
| DPro-spiroindole methyl-sulfonamide | 4 | 1.5 | <0.5 | 5.5 | 1.6 | 1.5 | 2.2 | 4.7 | 1.7 | 1.6 | 0.9 |
| DPro-pyrrolidine amide | 4 | 2.3 | 104 | 28 | 18 | 7.1 | 5.1 | 3.2 | 2.7 | 2.2 | 2.3 |
| | 4 | 2.1 | 63 | 32 | 45 | 30 | 11 | 6 | 4.9 | 4.1 | 3.6 |
| DPro-indole amide | 4 | 1.2 | 7 | 7.5 | 5.8 | 4.7 | 3.1 | 2.8 | 2.5 | 2 | 1.6 |
| DPro-3-piperidine methanol amide | 4 | 2.3 | 55 | 14 | 7.5 | 2.9 | 3.8 | 3.4 | 2.4 | 2.3 | 1.8 |
| DPro-tropinamide | 4 | 1.9 | 72 | 47 | 5.5 | 3.8 | 3.8 | 2.8 | 2.5 | 2.2 | 2.2 |
| DTrpPhe-Arg-5-amino pentamide | 2 | 3.1 | 83 | 20 | 6.8 | 3.9 | 2.9 | 3.3 | 3.1 | 3.3 | 3 |
| | 1 | 2.5 | 38 | 8.5 | 2.8 | 2.3 | 1.4 | 1.7 | 2.1 | 2 | 0.8 |

*Unless otherwise stated, R$^1$ is H

TABLE 6

In Vivo* Release of GH Rat

| | | | GHRP-2 | | | GH ng/ml | | | | | |
|---|---|---|---|---|---|---|---|---|---|---|---|
| # | Compound iv | control | .1 | .01 | .03 | .1 | .3 | 1 | 3 | 10 | 30 |
| 861 | inipDαNalDTrpNH$_2$ | 145 | 1251 | | | | | 485 | 2197 | 2380 | |
| 1473 | inipDαNalDValNH$_2$ | 145 | 1251 | | | | | 225 | | 225 | |
| 1466 | αAibDTrpDValNH$_2$ | 145 | 1251 | | | | | 124 | | 418 | |
| 1415 | αAibDTrpDProDSerNH$_2$ | 120 | 1465 | | | | 820 | 1658 | 2306 | 2896 | |
| 1417 | αAibDTrpDProDArgNH$_2$ | 120 | 1465 | | | | 1362 | | 2161 | 2057 | |
| 1246 | αAibDTrpDProDPheNH$_2$ | 92 | 566 | | | 203 | 594 | 1901 | 2339 | | |
| 1248 | αAibDTrpDProDTrpNH$_2$ | 145 | 1343 | | | | 229 | | 1814 | | |
| 1460 | αAibDTrpDValDValNH$_2$ | 145 | 1343 | | | | | 104 | | 240 | |

TABLE 6-continued

In Vivo* Release of GH Rat

|  |  |  | GHRP-2 |  |  | GH ng/ml |  |  |  |  |  |
|---|---|---|---|---|---|---|---|---|---|---|---|
| # | Compound iv | control | .1 | .01 | .03 | .1 | .3 | 1 | 3 | 10 | 30 |
| 1461 | αAibDValDProDValNH₂ | 145 | 1343 | | | | | 160 | | 261 | |
| 1464 | αAibDValDValDValNH₂ | 145 | 1343 | | | | | 96 | | 197 | |
| 1468 | αAibDTrpDProDLysNH₂ | 145 | 1343 | | | | 157 | | 791 | | |
| 1462 | αAibDProDProDValNH₂ | 145 | 1251 | | | | | 218 | | 185 | |
| 1472 | inipDαNalDTrpDValNH₂ | 145 | 1251 | | | 174 | 142 | 154 | 1019 | | |
| 1489 | αAibDTrpDProIleNH₂ | 135 | 1734 | | | 445 | 355 | 1884 | | | |
| 1476 | αγAbuDαNalDTrpDIleNH₂ | 166 | 1175 | | | 97 | 111 | 152 | 152 | | |
| 1495 | inipDαNalDTrpDProIleNH₂ | 166 | 1175 | | | | | 824 | | 1971 | |
| 1496 | inipDαNalDTrpPheIleNH₂ | 166 | 1175 | | | | | 1638 | | 2055 | |
| 1471 | inipDαNalDTrpDValArgNH₂ | 145 | 1251 | | | 98 | 184 | 843 | | | |
| 1469 | αAibDTrpDProDValDValNH₂ | 164 | 411 | | | | 783 | 2450 | 1975 | | |
| 1480 | αAibDTrpDProDProDPalNH₂ | 78 | 990 | | | 245 | 622 | 2775 | | | |
| 1481 | αAibDTrpDProDValArgDProNH₂ | 164 | 411 | | | 1703 | 2145 | 2278 | 2511 | | |
| 1484 | αAibDTrpDProDIleDArgNH₂ | 105 | 750 | 317 | 562 | 1863 | 2224 | 2446 | | | |
| 1475 | αγAbuDTrpDTrpDIleNH₂ | 101 | 369 | | | 123 | 125 | 113 | | | |
| 1486 | inipDαNalDTrpPheDValNH₂ | 101 | 369 | | | 203 | 352 | 1009 | | | |
| 1488 | αAibDTrpDProValNH₂ | 105 | 750 | | | 323 | 644 | 1725 | | | |
| 1465 | αAibDTrpDIleDIleNH₂ | 105 | 750 | | | | | 160 | | | |
| 1500 | αAibDTrpDProLeuNH₂ | 225 | 1429 | | | | 1831 | 2623 | | | |
| 1492 | αAibDTrpDProThrNH₂ | 164 | 411 | | | 125 | 176 | 1031 | | | |
| 1497 | DHisDTrpDProDValArgNH₂ | 164 | 411 | | | | 154 | 181 | 235 | 601 | |
| 1451 | DHisDTrpDProDThrNH₂ | 128 | 811 (.03) | | | | 1380 | 2450 | 3133 | 2731 | |
| | | 135 | 1734 | | | 898 | | | | | |
| 1452 | αAibDTrpDProDIleNH₂ | 105 | 750 | | | 1028 | 1837 | 2138 | | | |
| 1474 | αAibDTrpDPheDValNH₂ | 101 | 369 | | | 146 | 117 | 184 | | | |
| 1478 | αAibDTrpDProDValDArgNH₂ | 124 | 1251 | | | 1420 | 2304 | 2245 | | | |
| | | 135 | 1734 | | | 1177 | | | | | |
| 1293 | αAibDTrpDProDAlaNH₂ | 157 | 1171 | | | 416 | 341 | 1682 | 3295 | | |
| 1226 | αAibDTrpDProDProNH₂ | 124 | 1072 | | | | | 2129 | | | |
| 1136 | αAibDTrpDProArgNH₂ | 120 | 1465 | | | 297 | 670 | 1769 | 2644 | | |
| 1251 | αAibDTrpDProDValNH₂ | 188 | 439 | | 228 | 832 | 1581 | 2405 | | | |
| | | 120 | 1465 | | | 1584 | 2360 | 2181 | 3250 | | |
| 1325 | inipDαNalDTrpDProNH₂ | 120 | 1465 | | | | | 409 | 1203 | 2475 | |
| 1518 | αAibDαNalDProDValDArgNH₂ | 99 | 1179 | | | 298 | 722 | 1695 | 2279 | | |
| 1520 | αAibDαNalDProDIleDArgNH₂ | 99 | 1179 | | | 325 | 640 | 1481 | 2497 | | |
| 1487 | αAibDTrpDProDProDLysNH₂ | 135 | 1734 | | | 171 | 676 | 1562 | | | |
| 1506 | αAibHisDβNalDPheLysNH₂ | 136 | 1169 | | | 137 | 244 | 1416 | | | |
| 1507 | αAibHisDTrpDProDValNH₂ | 136 | 1169 | | | 129 | 94 | 118 | | | |
| 1508 | αAibHisDTrpDProDIleNH₂ | 136 | 1169 | | | 132 | 137 | 123 | | | |
| 1509 | αAibHisDTrpDProValArgNH₂ | 136 | 1169 | | | 157 | 138 | 123 | | | |
| 1510 | αAibHisDTrpDProDValArgNH₂ | 136 | 1169 | | | 145 | 133 | 246 | | | |
| 1511 | αAibDβNalDProDValNH₂ | 136 | 1169 | | | 171 | 246 | 486 | | | |
| 1512 | αAibDαNalDProDValNH₂ | 136 | 1169 | | | 143 | 141 | 611 | | | |
| 1523 | αAibDTrpDProDThrArgNH₂ | 99 | 1179 | | 1336 | 2219 | 2167 | 2781 | | | |
| 1524 | αAibDTrpDProDNleArgNH₂ | 99 | 1179 | | 1425 | 1952 | 2334 | 2164 | | | |
| | | 17 | 1395 | 298 | 1151 | 2593 | 2275 | 2672 | | | |
| 1525 | αAibDTrpDProDNValArgNH₂ | 99 | 1179 | | 1397 | 2061 | 2285 | 2250 | | | |
| | | 117 | 1395 | 146 | 580 | 1380 | 2047 | 1853 | | | |
| 1490 | αAibDTrpDProIleArgNH₂ | 135 | 1734 | | | 173 | 202 | 179 | | | |
| | | 105 | 750 | | | 137 | | 397 | | | |
| 1479 | αAibDTrpDProDProArgNH₂ | 101 | 369 | | | 2081 | 2566 | 2269 | | | |
| 1493 | αAibDTrpDProProArgNH₂ | 225 | 1429 | | | | 96 | 152 | 431 | | |
| 1483 | αAibDTrpDProDProDArgNH₂ | 135 | 1734 | | | 333 | | 1838 | | | |
| 1485 | αAibDTrpDProDIleArgNH₂ | 78 | 990 | 969 | 1472 | 1981 | 2073 | 3289 | | | |
| 1407 | αAibDTrpDProPheDSerNH₂ | 138 | 1004 | | | | | | | 389 | 1365 |
| 1137 | αAibDTrpDProPheArgNH₂ | 120 | 1465 | | | 225 | 175 | 149 | | | |
| 1470 | αAibDTrpDProDValArgNH₂ | 145 | 1251 | 600 | 1576 | 2647 | 2002 | 3414 | | | |
| 803 | SarDTrpDTrpPheArgNH₂ | 120 | 1465 | | | | 778 | 1894 | 2498 | | |
| 1532 | αAibDαNalDProDProArgNH₂ | 124 | 1012 | | | | | 1989 | | | |
| 1533 | αAibDαNalDProDNValArgNH₂ | 124 | 1012 | | | | | 1910 | | | |
| 1519 | αAibDαNalDProDIleArgNH₂ | 99 | 179 | | | 1641 | 1491 | 2354 | 2370 | | |
| 1521 | αAibDαNalDProDValLysNH₂ | 99 | 179 | | | 573 | 1372 | 2008 | 2355 | | |
| 1530 | αAibDαNalDProDThrArgNH₂ | 124 | 1012 | 388 | 317 | 1035 | 2873 | 2611 | | | |
| 1531 | αAibDβNalDProDThrArgNH₂ | 124 | 1012 | | | | | 2303 | | | |
| 1513 | αAibDβNalDProDValArgNH₂ | 136 | 1169 | | | 611 | 3230 | 3322 | | | |
| 1514 | αAibDαNalDProDValArgNH₂ | 136 | 1169 | | | 1508 | 2710 | 2562 | | | |
| | | 117 | 1395 | 404 | 687 | 1624 | 2516 | 2507 | | | |
| 1534 | αAibDTrpDProDNleNH₂ | 120 | 1132 | | | 436 | 718 | 1968 | | | |
| 1535 | αAibDTrpDProDNValNH₂ | 120 | 1132 | | | 228 | 614 | 1710 | | | |
| | αAibDTrpDProDIle-X | | | | | | | | | | |
| TJ 39 | 2-aminoethylamide | 124 | 1012 | | | 1416 | 1739 | 2742 | 2931 | | |
| TJ 49 | 5-aminopentylamide | 120 | 1132 | | | 1262 | 2822 | 2501 | 2426 | | |
| TJ 53 | 3-aminopropylamide | 120 | 1132 | | | 575 | 1697 | 2603 | 1901 | | |

TABLE 6-continued

In Vivo* Release of GH Rat

| # | Compound iv | GHRP-2 control | .1 | GH ng/ml .01 | .03 | .1 | .3 | 1 | 3 | 10 | 30 |
|---|---|---|---|---|---|---|---|---|---|---|---|
| | αAibDTrpDProDVal-X | | | | | | | | | | |
| TJ 45 | 2-aminoethylamide | 117 | 1395 | | | 813 | 1958 | 1736 | | | |
| TJ 6 | dimethylamide | 135 | 1734 | | | 247 | 836 | 1362 | 1805 | | |
| TJ 8 | diethylamide | 135 | 1734 | | | 232 | 255 | 366 | 1157 | | |
| | αAibDTrpDProDPro-X | | | | | | | | | | |
| TJ 28 | 2-aminoethylamide | 73 | 766 | | | 151 | 339 | 558 | 920 | 1999 | |
| 353 | DβNalAlaTrpDPheLysGlnGlyNH₂ | 90 | 1542 | | | 879 | 1307 | 1268 | 2729 | | |
| 359 | DAlaDTrpAlaTrpDPheLysValGlyNH₂ | 151 | | | | 2553 | 3653 | 2530 | | | |
| | | 90 | 1542 | | 452 | 1763 | 3364 | 3003 | | | |
| 371 | DAlaDβNalAlaTrpDPheLysGlnGlyGlyGlyNH₂ | 157 | 983 | 535 | 1834 | 2176 | 2116 | 3995 | | | |
| 356 | DAlaDTrpAlaTrpDPheLysHisGlyNH₂ | 90 | 1542 | | | 1252 | 2811 | 1886 | | | |

TABLE 7

In Vivo* Release of GH in Adult Beagle Dogs

| # | Compound | oral dose mg/kg | 0 | 0.5 | 1 | 2 | Time (hr) 3 Canine GH ng/ml | 4 | 5 | 6 | 7 | 8 |
|---|---|---|---|---|---|---|---|---|---|---|---|---|
| | αAibDTrpDProDIleX | | | | | | | | | | | |
| TJ49 | 5-aminopentylamide | 1 | 5.4 | 123 | 27 | 21 | 20 | 5.6 | 2.3 | 1.2 | 0.8 | 1.4 |
| | | 1 | 3.8 | 116 | 20 | 5.7 | 13 | 19 | 3.3 | 1.1 | 1 | 1.1 |
| TJ53 | 3-aminopropylamide | 1 | 6 | 44 | 19 | 22 | 7.8 | 6.4 | 6.7 | 5.4 | 6.4 | 6.9 |
| | | 1 | 5.9 | 91 | 32 | 19 | 7.3 | 6.2 | 13.2 | 6.6 | 4.7 | 5.6 |
| TJ39 | 2-aminoethylamide | 1 | 5.7 | 31 | 11 | 10 | 10 | 4 | 4.4 | 3.8 | 5.1 | 3.4 |
| | | 1 | 3.4 | 99 | 21 | 19 | 14 | 9.1 | 4.6 | 4 | 4.2 | 3.8 |
| TJ66 | 4-aminobutylamide | 1 | 1.8 | 100 | 20 | 19 | 4 | 2.8 | 2.7 | 2.1 | 3.4 | 2.8 |
| | αAibDTrpDProDValX | | | | | | | | | | | |
| TJ6 | N-dimethylamide | 1 | 5.1 | 9.5 | 5.4 | 5.6 | 5.5 | 6 | 6.2 | 5 | 6.4 | 3.8 |
| TJ8 | N-diethylamide | 1 | 20 | 8.7 | 5 | 15 | 6 | 4.4 | 4.8 | 5.1 | 4.3 | 4.4 |
| TJ45 | 2-aminoethylamide | 1 | 6.4 | 97 | 26 | 24 | 8 | 3 | 6 | 12 | 9 | 8 |
| | | 1 | 7.6 | 52 | 24 | 21 | 13 | 9 | 8 | 9 | 8 | 8 |
| | αAibDTrpDProDValX | | | | | | | | | | | |
| TJ61 | 5-aminopentylamide | 1 | 3.7 | 41 | 12 | 5.3 | 4.4 | 4.1 | 3.7 | 3.5 | 4.8 | 4.1 |
| | | 1 | 2.3 | 91 | 17 | 26 | 7.6 | 4.2 | 3.5 | 3 | 3.8 | 2.7 |
| | αAibDTrpDProDNleX | | | | | | | | | | | |
| TJ59 | 5-aminopentylamide | 1 | 6.4 | 54 | 16 | 13 | 5 | 5 | 5.1 | 6.9 | 6.4 | 5.9 |
| | | 1 | 6.7 | 112 | 19 | 14 | 13 | 7.4 | 6.6 | 7.1 | 6.4 | 5.4 |
| 1476 | αAibDTrpDProDValDArgNH₂ | 2 | 3.2 | 42 | 31 | 13 | 25 | 5 | 3.1 | 4.1 | 2.6 | 1.7 |
| 1513 | αAibDβNalDProDValArgNH₂ | 1 | 6.6 | 128 | 38 | 47 | 35 | 25 | 8.7 | 6.5 | 6.9 | 7.2 |
| | | 1 | 5.3 | 125 | 22 | 8.7 | 6.3 | 5 | 3.6 | 3.6 | 6.7 | 3.6 |
| 1514 | αAibDαNalDProDValArgNH₂ | 1 | 3.5 | 31 | 10 | 5.8 | 5.4 | 4.2 | 3.2 | 3.8 | 3.4 | 3.6 |
| | | 1 | 3.5 | 126 | 24 | 31 | 14 | 7.3 | 3.5 | 4.8 | 3.1 | 4.9 |
| 1519 | αAibDαNalDProDIleArgNH₂ | 1 | 6.8 | 72 | 28 | 21 | 13 | 6.5 | 5.5 | 4.4 | 6.9 | 5.2 |
| 1521 | αAibDαNalDProDValLysNH₂ | 1 | 3.7 | 111 | 39 | 61 | 29 | 14 | 8.2 | 4 | 4.4 | 4.7 |
| 973 | inipDαNalDβNalPheArgNH₂ | 2 | 3.1 | 13 | 4.2 | 3.3 | 2.5 | 2.1 | 2.9 | 2.3 | 2.9 | 2.4 |
| 1536 | αAibDTrpDProDIleArgGlyNH₂ | 0.5 | 1.5 | 93 | 23 | 29 | 8.2 | 6.5 | 5.5 | 4.3 | 4.3 | 2.9 |
| 1537 | αAibDTrpDProDNleArgGlyNH₂ | 0.5 | 3.7 | 76 | 12 | 10 | 2.6 | 3.1 | 2.3 | 2.3 | 2.8 | 2.8 |
| 1539 | αAibDTrpDProDThrArgGlyNH₂ | 0.5 | 1.8 | 86 | 28 | 85 | 13 | 7.6 | 4.8 | 2.7 | 2.7 | 2.3 |
| 1252 | αAibDTrpDProDGlnNH₂ | 2 | 1.5 | 2.6 | 6.4 | 3.5 | 2.8 | 2.5 | 2.3 | 1.9 | 1.9 | 2 |
| 869 | InipDαNalDTrpPheCOOH | 2 | 2.6 | 3.5 | 2 | 2.6 | 2.7 | 2.6 | 2.5 | 3.6 | 3.6 | 3.2 |
| | | 1 | 1.4 | 1.8 | 1.3 | 1.5 | 1.3 | 2.1 | 1.9 | 2.6 | 1.4 | 2.1 |
| 956 | InipDαNalDTrpValNH₂ | 1 | 4.2 | 3.3 | 3.9 | 4 | 3.6 | 5.5 | 3.4 | 3.8 | 2.3 | 3.1 |
| 1136 | αAibDTrpDProArgNH₂ | 1.1 | 4.9 | 15 | 8.3 | 6.3 | 4.8 | 5.2 | 4.8 | 4.3 | 5.1 | 4.8 |
| | | 1 | 1.7 | 27 | 8.7 | 1.5 | 1.9 | 1.9 | 2.4 | 2.7 | 1.6 | 2.7 |
| 1118 | αAibDTrpDProCHαAlaNH₂ | 1 | 6.6 | 3.8 | 2.6 | 2.6 | 2.8 | 2.8 | 1.9 | 2.1 | 2.9 | 2.6 |
| 1251 | αAibDTrpDProDValNH₂ | 2 | 2.9 | 47 | 16 | 14 | 7.8 | 5.6 | 4.7 | 5.6 | 6.8 | 4.9 |
| | | 2 | 1.6 | 28 | 5.6 | 4.1 | 4.1 | 4 | 4.1 | 4.2 | 3 | 2.6 |
| | | 1.1 | 2.4 | 128 | 31 | 42 | 5.5 | 4.8 | 4.4 | 3.4 | 4.4 | 3.4 |
| 1293 | αAibDTrpDProDAlaNH₂ | 2 | 4.6 | 11 | 4.9 | 4.9 | 4.6 | 5.5 | 5.9 | 4 | 4.7 | 4.7 |
| | | 2 | 2.9 | 15 | 8.9 | 11 | 4 | 3.8 | 3 | 2.7 | 3.6 | 2.7 |
| | | 2 | 3.9 | 14 | 6.2 | 3.8 | 2.7 | 1.9 | 2.9 | 2.4 | 3.4 | 3.1 |
| 1452 | αAibDTrpDProDIleNH₂ | 2 | 2.5 | 117 | 23 | 13 | 4.1 | 3.6 | 5 | 4.3 | 5.2 | 4.7 |
| 1451 | αAibDTrpDProDThrNH₂ | 2 | 1.4 | 20 | 4 | 3.9 | 2.7 | 2 | 1.7 | 2.5 | 2.6 | 1.6 |
| | | 1.6 | 3.3 | 51 | 22 | 58 | 7.1 | 5.6 | 4.9 | 4.6 | 4.6 | 4.1 |

TABLE 7-continued

In Vivo* Release of GH in Adult Beagle Dogs

| # | Compound | oral dose mg/kg | 0 | 0.5 | 1 | 2 | 3 | 4 | 5 | 6 | 7 | 8 |
|---|---|---|---|---|---|---|---|---|---|---|---|---|
| | | | | | | | Canine GH ng/ml | | | | | |
| 1246 | αAibDTrpDProDPheNH$_2$ | 2 | 1.7 | 29 | 20 | 9.2 | 3.7 | 2.7 | 1.6 | 1.9 | 2.4 | 1.8 |
| 1474 | αAibDTrpDPheDValNH$_2$ | 2 | 3.2 | 2.9 | 2.8 | 2.7 | 2.9 | 2.9 | 2.8 | 2.8 | 4.7 | 2.7 |
| 1248 | αAibDTrpDProDTrpNH$_2$ | 2 | 1.8 | 5.9 | 2.7 | 1.4 | 2.2 | 1.8 | 1.7 | 1.3 | 3.2 | 3.3 |
| 1479 | αAibDTrpDProDProArgNH$_2$ | 1.8 | 2 | 38 | 9.3 | 6.2 | 6.1 | 6 | 5.7 | 4.7 | 2.7 | 2.1 |
| 1478 | αAibDTrpDProDValDArgNH$_2$ | 2 | 3.2 | 42 | 31 | 13 | 25 | 5 | 3.1 | 4.1 | 2.6 | 1.7 |
| 1470 | αAibDTrpDProDValArgNH$_2$ | 2 | 3.6 | 62 | 26 | 30 | 30 | 6.8 | 13 | 14 | 6.5 | 5.4 |
| | | 2 | 3.4 | 37 | 32 | 41 | 13 | 23 | 9.2 | 8 | 4.9 | 4.1 |
| | | 1 | 5.1 | 32 | 14 | 18 | 16 | 14 | 11 | 6.3 | 6.3 | 5.2 |
| 1485 | αAibDTrpDProDIleArgNH$_2$ | 2 | 4.9 | 102 | 19 | 48 | 23 | 11 | 8 | 9 | 16 | 21 |
| | | 2 | 5.7 | 49 | 38 | 26 | 10 | 21 | 7.6 | 6.7 | 10 | 11 |
| | | 2 | 3.5 | 20 | 17 | 15 | 16 | 18 | 13 | 19 | 13 | 14 |
| | | 2 | 1.2 | 60 | 34 | 15 | 9.2 | | 5.3 | | 4.5 | 4.7 |
| | | 1 | 4.6 | 136 | 23 | 95 | 14 | 22 | 8.3 | 6.9 | 4.9 | 5.2 |
| | | 1 | 6.7 | 104 | 47 | 84 | 41 | 29 | 15 | 19 | 15 | 5.4 |
| | | 1 | 5.2 | 50 | 17 | 11 | 6.9 | 6.8 | 6.2 | 7.1 | 6.7 | 4.5 |
| | | 0.5 | 6 | 110 | 63 | 32 | 13 | 12 | 4.9 | 5 | 5.6 | 5.4 |
| | | 0.5 | 7.8 | 109 | 78 | 54 | 49 | 97 | 52 | 51 | 22 | 16 |
| | | 0.5 | 6.1 | 126 | 78 | 32 | 12 | 7.8 | 4.3 | 15 | 9.2 | 3.6 |
| | | 0.5 | 6.6 | 125 | 57 | 35 | 20 | 11 | 40 | 15 | 8 | 8 |
| | | 0.5 | 5.9 | 227 | 28 | 26 | 40 | 13 | 50 | 9 | 7 | 7 |
| | | 0.25 | 3.5 | 102 | 35 | 32 | 28 | 5.8 | 3.7 | 4.1 | 5 | 6.9 |
| | | 0.25 | 2.1 | 53 | 13 | 10 | | 3.1 | 2.1 | 4 | 3.3 | 4.4 |
| | | 0.125 | 3.6 | 48 | 23 | 7.9 | 3.8 | 3 | 3.9 | 3 | 5.7 | 3.4 |
| | | 0.125 | 2.6 | 53 | 16 | 7.6 | 3.3 | 3.9 | 3.9 | 3.6 | 5.3 | 3.2 |
| 1523 | αAibDTrpDProDThrArgNH$_2$ | 1 | 5.4 | 105 | 63 | 40 | 30 | 15 | 8 | 9.3 | 7.9 | 4 |
| 1524 | αAibDTrpDProDNleArgNH$_2$ | 1 | 5.3 | 110 | 105 | 128 | 38 | 25 | 18 | 7.8 | 4.5 | 3.8 |
| | | 0.5 | 5.6 | 72 | 23 | 10 | 7.1 | 7.1 | 6.7 | 6.4 | 5.9 | 5.6 |
| 1525 | αAibDTrpDProDNValArgNH$_2$ | 0.5 | 6 | 99 | 58 | 26 | 13 | 7.8 | 6.2 | 6 | 5.7 | 4.6 |
| TJ64 | 5-aminopentylamide | 1 | 1.5 | 32 | 13 | 5.6 | 3.5 | 2.3 | 2.7 | 1.4 | 2.9 | 3.2 |

What is claimed is:

1. A compound having the formula $A_{1''}$-Y, wherein $A_{1''}$ is Aib, inip, ABU, βAla, His, Sar (sarcosine) or any of their respective D-isomers;

Y is $A_{2'}$-$A_3$-$A_4$-$A_5$-$A_6$-Z';

$A_{2'}$-$A_3$-$A_4$-$A_5$-Z' or $A_{2'}$-$A_3$-$A_4$-Z';

wherein $A_{2'}$ is $A_5$-$A_{2''}$ or $A_{2''}$;

wherein $A_5$ is a spacer amino acid;

$A_{2''}$ is any natural L-amino acid, Pal (3-pyridylalanine), or their respective D-isomers, DαNal or DβNal;

$A_3$, $A_4$ and $A_5$ are any natural L-amino acid, Pal, αNal (alpha-napthylalanine), βNal (beta-napthlalanine), Nle, Arg-DPro, D-para-chlorophenlaline, D or L cyclohexyl-amino acid, or any of their respective D-isomers; and Z' is NH$_2$, OH, C$_1$–C$_{10}$ alkylamino, di(C$_1$–C$_{10}$ alkyl) amino, amino-C$_1$–C$_{10}$ alkylamino or di(amino C$_1$–C$_{10}$ alkyl) amino;

or a pharmaceutically acceptable salt thereof.

2. The compound of claim 1, having the formula Aib-Y.

3. The compound of claim 2, wherein the Aib residue is substituted or unsubstituted.

4. The compound of claim 2, wherein Aib is unsubstituted.

5. The compound of claim 1, wherein $A_{1''}$ is Aib, inip or ABU.

6. The compound of claim 1, wherein $A_{2''}$ is DTrp, DαNal or DβNal.

7. The compound of claim 6, wherein $A_{2''}$ is DTrp.

8. The compound of claim 1 or 6 wherein $A_3$ is DPro or DTrp.

9. The compound of claim 1 or 6, wherein $A_4$ is selected from the group consisting of Gly, Phe, Pro, Ile, DPro, DPhe, DPal, DLeu, DHis, DVal, DGln, DIle, DNle, DArg, DAla, DSer, DThr, DIle, Arg, Orn Lys, Ala, Pal, Thr, Val, Phe, DTrp, DNVal, DNle, D cyclohexylalanine and L cyclohexylalanine.

10. The compound of claim 8, wherein $A_4$ is selected from the group consisting of DPro, DTrp, DIle and DNle.

11. The compound of claim 1 or 6 wherein $A_5$ is selected from the group consisting of Ile, Arg, Pal, DArg, DSer, Lys or ArgDPro and DLys.

12. The compound of claim 10, wherein $A_5$ is selected from the group consisting of Arg, DArg, Lys and DLys.

13. The compound of claim 1 wherein Y is $A_{2''}$-DPro-$A_4$-$A_5$-A6-Z', $A_{2''}$-$A_3$-$A_4$-Z' or $A_{2''}$-$A_3$-$A_4$-$A_5$-Z'.

14. The compound of claim 2, wherein Y is $A_{2''}$-DPro-$A_4$-Z', or $A_{2''}$-DPro-$A_4$-$A_5$-Z'.

15. The compound of claim 2, wherein Y is $A_{2''}$-DPro-$A_4$-$A_5$-Z'.

16. The compound of claim 1, wherein said compound is selected from the group consisting of αAib-DTrp-DPro-$A_4$-$A_5$-$A_6$-Z', αAib-DTrp-DPro-$A_4$-$A_5$-Z', αAib-DTrp-DPro-$A_4$-Z', αAib-DTrp-DPro-$A_4$-Arg-NH$_2$, αAib-DTrp-DPro-$A_4$-Arg-$A_6$-NH$_2$, αAib-DTrp-DPro-$A_4$-Arg-Gly-NH$_2$, αAib-DαNal-DPro-$A_4$-$A_5$-$A_6$-Z', αAib-DαNal-DPro-$A_4$-$A_5$-Z', αAib-DαNal-DPro-$A_4$-Z', αAib-DαNal-DPro-$A_4$-NH$_2$, αAib-DαNal-DPro-$A_4$-Arg-NH$_2$, and αAib-DαNal-DPro-$A_4$-Arg-Gly-NH$_2$.

17. The compound of claim 1, wherein said compound is selected from the group consisting of inipDαNalDTrpNH$_2$, inipDαNalDValNH$_2$, αAibDTrpDValNH$_2$, αAibDTrpDProDSerNH$_2$, αAibDTrpDProDArgNH$_2$, αAibDTrpDProDPheNH₂, αAibDTrpDProDTrpNH₂,
αAibDTrpDValDValNH₂, αAibDValDProDValNH₂,
αAibDValDValDValNH₂, αAibDTrpDProDLysNH₂,
αAibDProDProDValNH₂, inipDαNalDTrpDValNH₂,
αAibDTrpDProIleNH₂, αγAbuDαNalDTrpDIleNH₂,
inipDαNalDTrpDProIleNH₂, inipDαNalDTrpPheIleNH₂,
inipDαNalDTrpDValArgNH₂,
αAibDTrpDProDValDValNH₂,
αAibDTrpDProDProDPalNH₂,
αAibDTrpDProDValArgDProNH₂,
αAibDTrpDProDIleDArgNH₂, αγAbuDTrpDTrpDIleNH₂,
inipDαNalDTrpPheDValNH₂, αAibDTrpDProValNH₂;
αAibDTrpDIleDIleNH₂, αAibDTrpDProLeuNH₂,
αAibDTrpDProThrNH₂, DHisDTrpDProDValArgNH₂,
DHisDTrpDProDThrNH₂, αAibDTrpDProDIleNH₂,
αAibDTrpDPheDValNH₂, αAibDTrpDProDValDArgNH₂,
αAibDTrpDProDAlaNH₂, αAibDTrpDProDProNH₂,
αAibDTrpDProArgNH₂, αAibDTrpDProDValNH₂,
inipDαNalDTrpDProNH₂,
αAibDαNalDProDValDArgNH₂,
αAibDαNalDProDIleDArgNH₂,
αAibDTrpDProDProDLysNH₂,
αAibHisDαNalDProDPheLysNH₂,
αAibHisDTrpDProDValNH₂, αAibHisDTrpDProDIleNH₂,
αAibHisDTrpDProValArgNH₂,
αAibHisDTrpDProDValArgNH₂,
αAibDαNalDProDValNH₂, αAibDTrpDProDThrArgNH₂,
αAibDTrpDProDNleArgNH₂,
αAibDTrpDProDNValArgNH₂,
αAibDTrpDProIleArgNH₂, αAibDTrpDProDProArgNH₂,
αAibDTrpDProProArgNH₂,
αAibDTrpDProDProDArgNH₂,
αAibDTrpDProDIleArgNH₂, αAibDTrpDProPheDSerNH₂,
αAibDTrpDProPheArgNH₂, αAibDTrpDProDValArgNH₂,
SarDTrpDTrpPheArgNH₂, αAibDαNalDProDProArgNH₂,
αAibDαNalDProDNValArgNH₂,
αAibDαNalDProDIleArgNH₂,
αAibDαNalDProDValLysNH₂,
αAibDαNalDProDThrArgNH₂,
αAibDαNalDProDThrArgNH₂,
αAibDαNalDProDValArgNH₂,
αAibDαNalDProDValArgNH₂, αAibDTrpDProDNleArgNH₂,
αAibDTrpDProDNValNH₂, αAibDTrpDProDProArgNH₂,
αAibDTrpDProDValDArgNH₂,
αAibDTrpDProDValArgNH₂,
αAibDTrpDProDIleArgNH₂,
αAibDαNalDProDValArgNH₂,
αAibDαNalDProDValArgNH₂,
αAibDαNalDProDIleArgNH₂,
αAibDαNalDProDValLysNH₂,
inipDαNalDαNalPheArgNH₂,
αAibDTrpDProDThrArgNH₂,
αAibDTrDProDNleArgNH₂,
αAibDTrpDProDNValArgNH₂,
αAibDTrpDProDIleArgGlyNH₂,
αAibDTrpDProDProDIleArgGlyNH₂,
αAibDTprDProDNleArgGlyNH₂,
αAibDTrpDProDThrArgGlyNH₂,
αAibDTrpDProDProA₄ArgNH₂,
αAibDTrpDProDProA₄ArgGlyNH₂,
αAibDTrpDProDIleArgNH₂,
αAibDTrpDProDIleArgGlyNH₂,
αAibDTrpDProDProDIleArgNH₂,
αAibDTrpDProDProDIleArgGlyNH₂,
DβNalAlaTrpDPheLysGlnGlyNH₂,
DAlaDTrpAlaTrpDPheLysValGlyNH₂,
DAlaDβNalAlaTrpDPheLysGlnGlyGlyGlyNH₂,
DAlaDTrpAlaTrpDPheLysHisGlyNH₂, and αAibDTrpD-
ProDNleArgGlyNH₂.

18. A compound of the formula $A_1$-$A_2$-X, wherein $A_1$ is Aib, inip or ABU; $A_2$ is any natural L-amino acid or Pal, or their respective D-isomers, DαNal or DβNal; and X is
(1) $R_1$-$R_2$-Z, wherein $R_1$ and $R_2$ are any natural L-amino acid, Pal, αNal, βNal, D-para-cholophenylalanine, CHx, where $CH_x$ is cyclohexyl, CHxAla, or any of their respective D-isomers; and Z is $CONH_2$ or COOH;
(2) D-(para-$R_3$Phe)-$R_4$-Z, wherein $R_3$ is a halogen; $R_4$ is L-amino acid or Pal, or their respective D-isomers; and Z is $CONH_2$ or COOH;
(3) $NH(CH_2)_n NH$, where n is 1 to 8;
(4) $R_5$-$R_6$, wherein $R_5$ is any natural L-amino acid, Pal, αNal, βNal, DpCl, CHx, or any of their respective D-isomers; and $R_6$ is diisobutylamide, dipropylamide, butylamide, pentylamide, dipentylamide, or C(=O)(substituted heteroalicyclic or heteroaromatic);
(5) DTrp Phe Arg$R_7$, wherein $R_7$ is $NH(CH_2)_n NH$, where n is 1 to 8; or
(6) $R_8$-$R_9$-$R_{10}$-Z, wherein $R_8$ is DTrp, DPro, DαNal or DβNal; $R_9$ is any natural L-amino acid or Pal, or their respective D-isomers; $R_{10}$ is any natural L-amino acid or Pal, or their respective D-isomers; and Z is $CONH_2$ or COOH, on a pharmaceutically acceptable salts thereof; or of the formula $A_1'$-X', wherein $A_1'$ is Aib (aminoisobutyric acid), inip (isonipecotyl), ABU (aminobutyric acid), βAla, Ileu, Trp, His, DpCl, CHx where $CH_x$ is cyclohexyl, or any of their respective D-isomers; and X' is
(1) $R_1'$-$R_2'$-Z', wherein $R_1$ is any natural L-amino acid or Pal, or their respective D-isomers, DαNal or DβNal; and R2 is any natural L-amino acid, Pal, αNal, βNal, DpCl, Aib, CHx, or CHxAla, or any of their respective D-isomers; and Z is $CONH_2$ or COOH; or
(2) $R_3$-$R_4$, wherein $R_3$ is any natural L-amino acid or Pal, or their respective D-isomers, DαNal or DβNal; and $R_4$ is $NH(CH_2)_n NH$, where n is 1 to 8, or a pharmaceutically acceptable salt thereof.

19. The compound of claim 18, wherein $A_1$ or $A_1'$ is αAib, and $A_2$ $A_2'$ is selected from the group consisting of DTrp and DαNal.

20. A pharmaceutical composition comprising a compound of claim 1 or 18 and the pharmaceutically acceptable carrier or diluent.

21. The pharmaceutical composition of claim 20, which further comprises a second compound which acts as an agonist at the growth hormone releasing hormone receptor or inhibits the effects of somatostatin.

* * * * *